US008055512B1

(12) United States Patent
Pankow et al.

(10) Patent No.: US 8,055,512 B1
(45) Date of Patent: Nov. 8, 2011

(54) MANIFEST, METHODS AND SYSTEMS FOR MULTI-DOSE MEDICATION ORDER FILL

(75) Inventors: Greg Pankow, Morton Grove, IL (US); Sean McGonagle, Buffalo Grove, IL (US); Amy C. Biesenthal, Buffalo Grove, IL (US)

(73) Assignee: Walgreen Co., Deerfield, IL (US)

( * ) Notice: Subject to any disclaimer, the term of this patent is extended or adjusted under 35 U.S.C. 154(b) by 388 days.

(21) Appl. No.: 12/275,436

(22) Filed: Nov. 21, 2008

(51) Int. Cl.
*G06Q 10/00* (2006.01)
*G06Q 50/00* (2006.01)
(52) U.S. Cl. .......................................... 705/2
(58) Field of Classification Search ............... 705/2, 3; 395/203
See application file for complete search history.

(56) References Cited

U.S. PATENT DOCUMENTS

| | | | |
|---|---|---|---|
| 5,208,762 A | | 5/1993 | Charhut et al. |
| 5,737,539 A | * | 4/1998 | Edelson et al. ............... 705/3 |
| 5,771,657 A | | 6/1998 | Lasher et al. |
| 6,769,228 B1 | | 8/2004 | Mahar |
| 7,025,207 B2 | | 4/2006 | Breu et al. |
| 2003/0216974 A1 | | 11/2003 | Browne |
| 2004/0148054 A1 | | 7/2004 | Schwartz |
| 2004/0215486 A1 | * | 10/2004 | Braverman ................... 705/2 |
| 2005/0004700 A1 | | 1/2005 | DiMaggio |
| 2005/0065645 A1 | | 3/2005 | Liff et al. |
| 2006/0074521 A1 | | 4/2006 | Rice et al. |
| 2006/0149587 A1 | | 7/2006 | Hill et al. |
| 2006/0161294 A1 | | 7/2006 | DiMaggio |
| 2006/0161298 A1 | | 7/2006 | DiMaggio |
| 2007/0067250 A1 | | 3/2007 | Mahar |
| 2007/0095850 A1 | | 5/2007 | Meyer |
| 2007/0185615 A1 | | 8/2007 | Bossi et al. |
| 2007/0250346 A1 | | 10/2007 | Luciano, Jr. et al. |
| 2008/0071421 A1 | | 3/2008 | Silverbrook et al. |
| 2008/0097787 A1 | * | 4/2008 | Palazzolo et al. ............ 705/2 |
| 2008/0265011 A1 | | 10/2008 | Specker |

FOREIGN PATENT DOCUMENTS

| | | |
|---|---|---|
| EP | 1270441 | 1/2003 |
| WO | WO02100736 | 12/2002 |
| WO | WO2005023672 | 3/2005 |

OTHER PUBLICATIONS

"What is Medicine On Time?" <http://www.medicine-on-time.com/>, Medicine-On-Time University, 2008.
"Product Line" <http://www.medicine-on-time.com/>, Medicine-On-Time University, 2008.

* cited by examiner

*Primary Examiner* — Gerald J. O'Connor
*Assistant Examiner* — John Pauls
(74) *Attorney, Agent, or Firm* — Francis C. Kowalik; Marshall, Gerstein & Borun LLP

(57) ABSTRACT

A manifest for a multi-dose medication order is disclosed. The manifest may serve as a single recipe or roadmap for the prescriptions and containers required for a multi-dose medicament order. The manifest may include a representation of intersecting prescription and container matrices, with each intersecting entry including an indication of a number of medicaments of an individual prescription mapped to be packaged into an individual container. Machine-readable identifiers and fields for different levels of approval may be included on the manifest. Dosing regime parameters may be visually differentiated. Methods and systems for creating a manifest and using the manifest in filling a multi-dose medicament order are also disclosed.

44 Claims, 11 Drawing Sheets

Fig. 1

MultiDose Order #111111111

| Rx # | Medication Name NDC # | Directions | Weeks 1,2,3,4 Morning(1) | Weeks 1,2,3,4 Morning(2) | Weeks 1,2,3,4 Night | Total # Tabs | Lot# Exp Date | Initial Tech/RPh 522 | Prescription Bar Code 525 |
|---|---|---|---|---|---|---|---|---|---|
| 11111 520a | HYDROCHLOROTHIAZIDE 25MG 00228-2221-96 | T QAM, TT HS | 30/1x 532a | | 60/2x 534a | 90 | | | |
| 22222 520b | BrandName1 10MG TABLETS 00224-5421-31 | TT HS | | | 60/2x 534b | 60 | | | |
| 33333 520c | BrandName2 10MG TABLETS 00071-0155-23 | T AM | 30/1x 532c | | | 30 | | | |
| 44444 520d | BrandName3 40MG CAPSULES 00186-5040-31 | TT QAM, TT HS | 60/2x 532d | | 60/2x 534d | 120 | | | |
| 55555 520e | GenericName1 10MG TABLETS 00069-5510-66 | T BID | 30/1x 532e | | 30/1x 534e | 60 | | | |
| 66666 520f | IBUPROFEN 800MG TABLETS 00591-3466-05 | TTT QAM IV Q HS | | 90/3x 533a | 120/4x 534f | 210 | | | |
| | Total Pills per Blister | | 5 | 3 | 11 | | | | |

Filled Date: 11/1/2008
Card Start Date: 11/11/2008
John Doe
111 E Street Rd
Chicago, IL 60111
312-111-1111

Week 1
Week 2
Week 3
Week 4

Tech: _____
RPh: _____
Order Complete

Fig. 5

| Rx # | Medication Name NDC # | Directions | Week 1 Morning(1) | Week 1 Morning(2) | Week 1 Noon | Week 1 Evening | Week 1 Night | Total # Tabs | Lot# Exp Date | Initial Tech/RPh | Prescription Bar Code |
|---|---|---|---|---|---|---|---|---|---|---|---|
| 11111 | HYDROCHLOROTHIAZIDE 25MG 00228-2221-96 | T QAM, TT HS | 7  1x ⒻⒷ | | | | 14  2x ⒻⒷ | 21 | | | |
| 22222 | BrandName1 10MG TABLETS 00224-5421-31 | TT HS | | | | | 14  2x ⒸⒹ | 14 | | | |
| 33333 | BrandName2 10MG TABLETS 00071-0155-23 | T AM | 7  1x ⒸⒹ | | | | | 7 | | | |
| 44444 | BrandName3 40MG CAPSULES 00186-5040-31 | TT QID | 14  2x ⒺⒷ | | 14  2x ⒺⒷ | 14  2x ⒺⒷ | 14  2x ⒻⒷ | 56 | | | |
| 55555 | GenericName1 10MG TABLETS 00069-5510-66 | T BID | 7  1x ⒻⒷ | | | | 7  1x ⒻⒷ | 14 | | | |
| 66666 | IBUPROFEN 800MG TABLETS 00591-3466-05  608 | TTT QAM IV Q HS | | 21  3x  | | | 28  4x ⒺⒷ | 49 | | | |
| | Total Pills per Blister | | 5 | 3 | 2 | 2 | 11 | | | | |

Filled Date: 11/1/2008
Card Start Date: 11/11/2008
John Doe
111 E Street Rd
Chicago, IL 60111
312-111-1111

MultiDose Order #1111111111

Fig. 6A

| Rx # | Medication Name NDC # | Directions | Week 2 Morning(1) | Week 2 Morning(2) | Week 2 Noon | Week 2 Evening | Week 2 Night | Total # Tabs | Lot # Exp Date | Initial Tech/RPh | Prescription Bar Code |
|---|---|---|---|---|---|---|---|---|---|---|---|
| 11111 | HYDROCHLOROTHIAZIDE 25MG 00228-2221-96 | T QAM, TT HS | 7̲ 1x ⒺⒷ | | | | 1̲4̲ 2x ⒻⒷ | 21 | | | |
| 22222 | BrandName1 10MG TABLETS 00224-5421-31 | TT HS | | | | | 1̲4̲ 2x ⒻⒸⒷ | 14 | | | |
| 33333 | BrandName2 10MG TABLETS 00071-0155-23 | T AM | 7̲ 1x ⒻⒷ | | | | | 7 | | | |
| 44444 | BrandName3 40MG CAPSULES 00186-5040-31 | TT QID | 1̲4̲ 2x ⒻⒷ | | 1̲4̲ 2x ⒻⒷ | 1̲4̲ 2x ⒻⒷ | 1̲4̲ 2x ⒻⒷ | 56 | | | |
| 55555 | GenericName1 10MG TABLETS 00069-5510-66 | T BID | 7̲ 1x ⒻⒷ | | | | 7̲ 1x ⒻⒷ | 14 | | | |
| 66666 | IBUPROFEN 800MG TABLETS 00591-3466-05 | TTT QAM IV Q HS | | 2̲1̲ 2x ⒻⒷ | | | 2̲8̲ 2x ⒻⒷ | 28 | | | |
| | Total Pills per Blister | | 5 | 3 | 2 | 2 | 11 | | | | |

Filled Date: 11/1/2008
Card Start Date: 11/11/2008
John Doe
111 E Street Rd
Chicago, IL 60111
312-111-1111

MultiDose Order #1111111111 

Fig. 6B

| Rx # | Medication Name NDC # | Directions | Picture | MultiDose Order #11111111 | | Total # Tabs | Lot# Exp Date | Initial Tech/RPh | Prescription Bar Code |
|---|---|---|---|---|---|---|---|---|---|
| | | | | Card 1 of 2 Morning | Card 2 of 2 Night | | | | |
| 11111 710a | HYDROCHLOROTHIAZIDE 25MG 0228-2221-96 | T QAM, TT HS | F B | 30 712a ●●●● ●●●● ●●●● ●●●● ●●●● ●●●● ●●●● | 60 ●●●● ●●●● ●●●● ●●●● ●●●● ●●●● ●●●● | 90 | | | |
| 22222 710b | BrandName1 10MG TABLETS 00224-5421-31 | TT HS | F B | 712b | 60 ●●●● ●●●● ●●●● ●●●● ●●●● ●●●● ●●●● | 60 | | | |
| 33333 710c | BrandName2 10MG TABLETS 00071-0155-23 | T AM | F B | 30 712c ●●●● ●●●● ●●●● ●●●● ●●●● ●●●● ●●●● | | 30 | | | |
| 44444 710d | BrandName3 40MG CAPSULES 00186-5040-31 | T QoD | F B | 30 712d ●●●● ●●●● ●●●● ●●●● ●●●● ●●●● ●●●● | | 60 | | | |
| | 715 | | Total Pills per Blister | 3 | 4 ← 705 | | | | |

Filled Date: 11/1/2008
Card Start Date: 11/11/2008
John Doe
111 E Street Rd
Chicago, IL 60111
312-111-1111

Order Complete
Tech:
RPh:

Fig. 7

MultiDose Order #111111111

| Rx # | Medication Name NDC # | Directions | Card 1 Week 1 Time of Day AM | Card 1 Week 1 Time of Day PM | Card 1 Week 2 Time of Day AM | Card 1 Week 2 Time of Day PM | Card 2 Week 3 Time of Day AM | Card 2 Week 3 Time of Day PM | Card 2 Week 4 Time of Day AM | Card 2 Week 4 Time of Day PM | Total # Tabs | Lot# Exp Date | Initial Tech/RPh | Prescription Bar Code |
|---|---|---|---|---|---|---|---|---|---|---|---|---|---|---|
| 11111 1018a | HYDROCHLOROTHIAZIDE 25MG 00228-2221-96 | T QAM, TT HS | 1 ○ | 2 ○ | 1 ○ | 2 ○ | 1 ○ | 2 ○ | 1 ○ | 2 ○ | 90 | | / | |||||||| |
| 22222 1018b | BrandName1 10MG TABLETS 00224-5421-31 | TT HS | | 2 ▢ | | 2 ▢ | | 2 ▢ | | 2 ▢ | 60 | | / | |||||||| |
| 33333 1018c | BrandName2 10MG TABLETS 00071-0155-23 | T AM | 1 ▢ | | 1 ▢ | | 1 ▢ | | 1 ▢ | | 30 | | / | |||||||| |
| 44444 1018d | BrandName3 40MG CAPSULES 00186-5040-31 | TT QID | 1 ⊟ | 2 ⊟ | 1 ⊟ | 2 ⊟ | 1 ⊟ | 2 ⊟ | 1 ⊟ | 2 ⊟ | 90 | | / | |||||||| |
| 55555 1018e | GenericName1 10MG TABLETS 00069-5510-66 | T BID | 1 ○ | 1 ○ | 1 ○ | 1 ○ | 1 ○ | 1 ○ | 1 ○ | 1 ○ | 60 | | / | |||||||| |
| 66666 1018f | IBUPROFEN 800MG TABLETS 00591-3466-05 | TTT QAM IV Q HS | 3 ⊟ | 4 ⊟ | 3 ⊟ | 4 ⊟ | 3 ⊟ | 4 ⊟ | 3 ⊟ | 4 ⊟ | 210 | | | |||||||| |
| Total Pills per Blister | | | 7 | 11 | 7 | 11 | 7 | 11 | 7 | 11 | | | | |

Filled Date: 11/1/2008
Card Start Date: 11/11/2008
John Doe
111 E Street Rd
Chicago, IL 60111
312-111-1111

Order Complete
Tech: _____
RPh: _____

Fig. 10

MANIFEST, METHODS AND SYSTEMS FOR MULTI-DOSE MEDICATION ORDER FILL

FIELD AND BACKGROUND OF THE DISCLOSURE

1. Field of the Disclosure

This disclosure relates generally to a manifest, methods and systems for the filling of a multi-dose medicament order.

2. Background Description

Multi-dose medicament containers, such as multi-dose blister containers or multi-dose rolls of pouches, are commonly known in the art. A multi-dose medicament container may contain the medicaments from a set of prescriptions of a multi-dose medicament order for a patient, with the medicaments packaged into a configuration or fill pattern that is convenient and useful for the patient. For example, a blister of a multi-dose blister pack may contain a set of units of medicaments from a set of patient's prescriptions that are to be ingested each morning. A second blister may contain a different set of units of medicaments that are to be ingested at noon, and a third blister may contain a yet different set of units of medicaments to be ingested at night. This combination of three types of blister fills may be repeated for every day of a week, and a multi-dose blister pack may contain a week's worth of medicaments and be labeled for a specific week. A patient may easily separate an individual blister for a particular time of ingestion of a particular day of a particular week, and have the correct, portable set of medicament units for ingestion.

In another example, a similar configuration may be implemented using multi-dose rolls of pouches, where a roll may contain a week's worth of medicaments divided into multiple pouches, with each day's medicaments contained in a single pouch. A patient may easily separate an individual pouch to have the correct, portable set of medicament units for ingestion.

Of course, as commonly known, the configuration or multi-dose fill pattern of a multi-dose medicament container is not limited to packaging by a time period of ingestion. Other fill patterns are also possible and known in the art. Independent of a specific fill pattern, however, the fill process of a multi-dose medicament order itself can be confusing and difficult to administrate and verify. The fill process requires a number of medicaments from each individual prescription to be selected and packaged into a specific receptacle of a multi-dose medicament container, and then this must be repeated for each individual prescription that has a medicament mapped to be packaged into the same receptacle. A different combination of individual prescriptions may need to be selected and packaged for each different receptacle of the container. For a single prescription, the fill process is simple. For a multi-dose medicament order, however, the fill process may quickly become unwieldy.

For example, currently, multi-dose medicament order fills are generally prescription-based. That is, each individual prescription in the multi-dose medicament order may have a separate physical or electronic representation or record, and the entire order may typically be viewed as a combination of these prescription records. A person or other filling entity is required to decipher multiple records in order to perform steps to fill a specific receptacle of a multi-dose medicament order, and then again re-access the same multiple records to fill a different receptacle. The multiple records again must be accessed at the end of the fill for verification of each of the receptacles. Given a multitude of receptacles in a multitude of containers, the fill process may quickly become difficult to manage.

Additionally, if different parties are responsible for different steps of the fill, the multiple records must be passed along, thus increasing the chance of inadvertent omission or error. Also with multiple different parties, determining the status of progress of a multi-dose medicament fill (e.g., which prescriptions have already been filled, and which have not yet been filled, which containers have already been filled, and which have not yet been filled, etc.) may also be difficult and confusing.

Furthermore, the determination and verification of the number of different types of prescription medicaments that are packaged into a receptacle of a multi-dose medicament container may be cumbersome. Again, this information must be aggregated from multiple sources. The identification of the medicaments are typically by alphanumeric names, which are difficult to spell, remember, and match to a specific packaged medicament for verification.

Moreover, filling a multi-dose medicament order may be even more complex given the plethora of filling machines and processes in the art. These filling machines and processes range from virtually manual (e.g. pharmacist in a store-front pharmacy) to virtually automatic (e.g., high-speed, centrally located filling machines). Managing the administration and verification of a multi-dose medicament order becomes more difficult and unwieldy with the variety of different filling systems and processes.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Embodiments of a single manifest for a multi-dose medicament order are disclosed. A "multi-dose medicament order," as used herein, is a direction or request to provide one or more prescriptions of a patient in a multi-dose medicament container, such as a multi-dose container or a multi-dose roll of pouches. A manifest generally may be a representation of the multi-dose medicament order in printed or electronic form. The representation may include an intersection of at least two matrices, with one matrix corresponding to the set of prescriptions in the multi-dose medicament order and one matrix corresponding to the set of containers in the multi-dose medicament order. The contents of the entries or fields at the intersection of the matrices may indicate a number of medicaments of an individual prescription mapped to be packaged into an individual container.

Embodiments of the single manifest may include various useful characteristics that aid to optimize the fill process. For example, the indications of the number of medicaments may be in a pictorial format. The representation of different dosing regime parameters may be visually differentiated. Inter-related machine-readable identifiers at a prescription, container, and order level may be provided. Approval fields may also be provided at a prescription, container, and order level.

Embodiments of methods for creating a single manifest for a multi-dose medicament order are disclosed. The methods may obtain multi-dose medicament order information, prescription information, container information and fill pattern information, and may consolidate these sets of information into a manifest. The manifest may be displayed or sent to another entity for use.

Embodiments of methods for using a single manifest for a multi-dose medicament order fill are disclosed. The methods may obtain a manifest and may use the manifest in performing one or more steps of filling the multi-dose medicament order. These steps may include, for example, initiating printing of the order, selecting medicaments from inventory, order verification, as well as other steps used in filling a multi-dose medicament order.

Embodiments of systems that support the creation and the use of a manifest for a multi-dose medicament order fill are disclosed. The systems may include a computer that is operatively connected to one or more storage entities, picking entities, filling entities, verification entities, and networks. In some embodiments, the computer itself may serve as one or more of the above entities. Embodiments of the systems may support any range of automation of a multi-dose medicament order fill, from totally manual to totally automatic.

BRIEF DESCRIPTION OF SEVERAL VIEWS OF THE DRAWING

FIG. 1 is an embodiment of a manifest for a multi-dose medicament order;

FIGS. 5-10 each illustrate a different embodiment of a manifest, with each different embodiment corresponding to a different multi-dose medicament order having a different combination of intersecting dosing regimes.

DETAILED DESCRIPTION OF THE PREFERRED EMBODIMENTS

Figure 2:
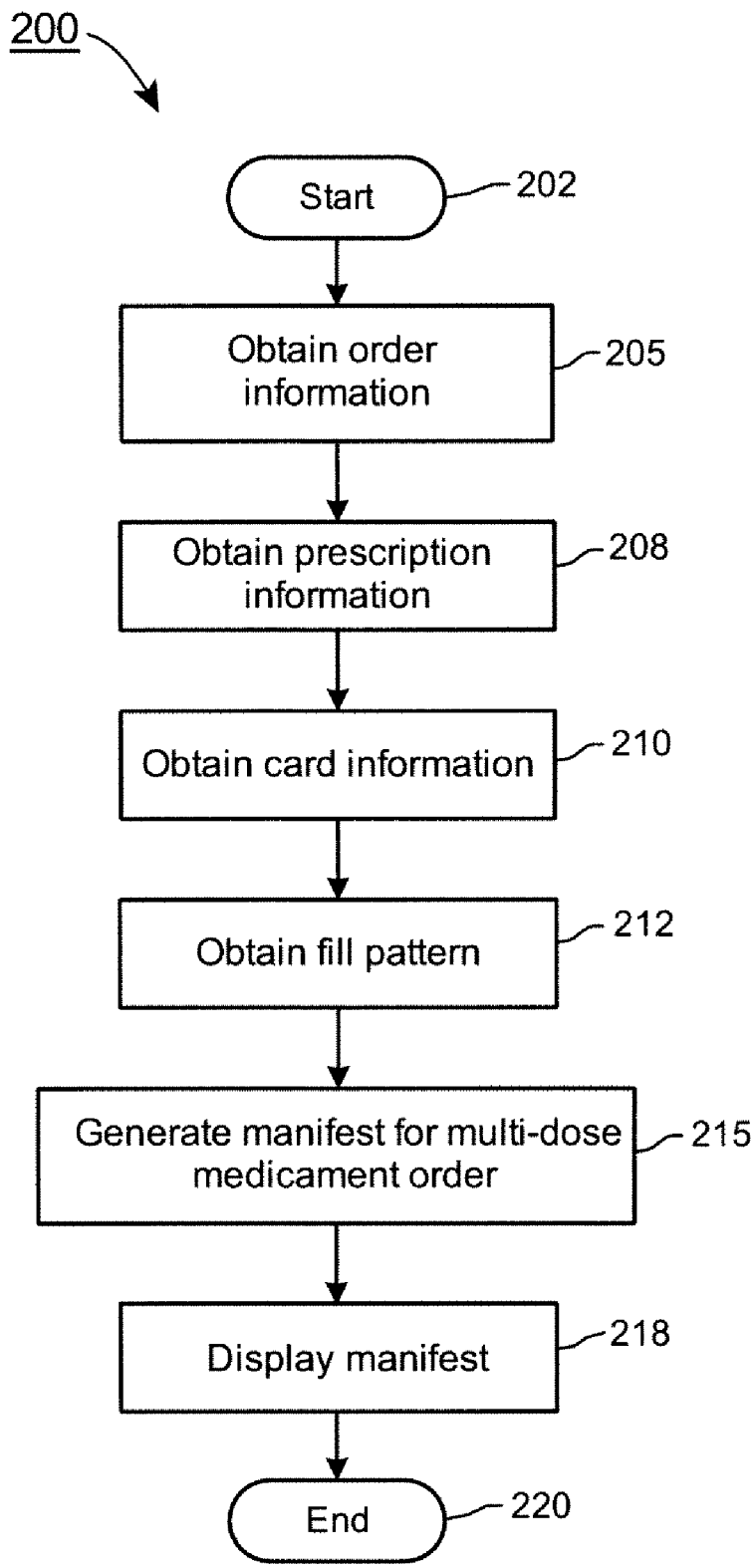
FIG. 2 is an embodiment of a method for creating a manifest for a multi-dose medicament order.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Before describing the figures of the disclosure, a description of terms and concepts used within the present disclosure is in order. A "multi-dose medicament order," as used herein, is a direction or request to provide one or more prescriptions of a patient in a multi-dose container format. A set of prescriptions for a patient may be filled into a set of multi-dose containers. Typically, but not necessarily, the one or more prescriptions may have overlapping dosing regimes, e.g., an intersection of dosing regimes that allows one or more pills from various prescriptions of the set of prescriptions that may be packaged together. A "dosing regime" may be an indication of how and when to take pills in accordance with the prescription directions. In addition to prescribed medications, multi-dose medicament orders may include, for example, nutraceuticals, over-the-counter (OTC) medications, or some combination thereof.

The term "prescription," as used herein, is not only limited to a direction by a physician to a pharmacist for the preparation and use of a medicine or remedy. The term "prescription" as used herein may also refer to a nutraceutical that the patient is taking, an OTC medication that the patient is taking, or some combination of one or more of an OTC medication, nutraceutical and/or prescribed medication for the patient.

A multi-dose medicament order may be packaged into a multi-dose medicament container. Multi-dose medicament containers may be available in different types. For instance, a multi-dose blister pack may be one type of multi-dose medicament container used to fill one or more prescriptions for a patient. Examples of multi-dose blister packs may be found, for instance, in U.S. patent application Ser. No. 12/130,365 entitled "Multi-Dose Blister Card Pillbook." In another example, a multi-dose medicament container may be a roll of individual pouches that are perforated so that the individual pouches may be easily separated from the roll. In another embodiment, a multi-dose medicament container may be a single receptacle or cell with multiple medicaments contained therein. Other embodiments of multi-dose containers may be possible, and may be used in accordance with the present disclosure.

Multi-dose blister containers may be perforated into individual, easily-portable receptacles, such as receptacles or pouches. The receptacles for a single multi-dose container may be similarly sized, or receptacles may be sized differently for a single multi-dose container. Each receptacle may be labeled to identify different medications contained within the receptacle, and may also list patient information, time/day/date information for ingestion and/or other dosing regime instructions, and the like. A patient may conveniently separate out from the container only the specific receptacles that s/he will need during a specific time period. The patient is not required to sort out the dosages of multiple medications for each medication's dosing regime. Additionally, the labeling on the receptacles and/or containers may aid the patient in keeping track of whether medications have been taken.

One or more multi-dose containers may be used to fill a multi-dose medicament order for a patient. A "fill pattern," as used herein, is defined as a mapping of pills from one or more prescriptions of a patient into one or more receptacles of one or more multi-dose medicament containers. Fill patterns may be complex. For example, in the case of a container containing one week's dosage of prescriptions, if Prescription A is required to be ingested once a day, and Prescription B is required to be ingested twice a day, the fill pattern may perform the appropriate mapping so that each labeled receptacle of the container contains the appropriate combination of pills. A "Monday morning," "Tuesday morning," "Wednesday morning" and other "morning" receptacles may be mapped to contain two pills, one of Prescription A and one of Prescription B. A "Monday evening," "Tuesday evening," and other "evening" receptacles may be mapped to contain only one of Prescription B's pills.

In another example of a multi-dose medicament order fill pattern, a multi-dose container, for instance, may be labeled "morning," so that each individual receptacle on the "morning" container may contain the complete set of pills from a patient's one or more prescriptions that are to be ingested in the morning. Additional filled, multi-dose containers labeled "noon" and "night" may also be included with the multi-dose medicament order fill, with the "noon" container having individual receptacles each containing the correct multiple medications to be ingested at "noon", and the "night" container having receptacles each containing the correct multiple medications to be ingested at "night."

In addition to the above examples, other configurations or fill patterns may be used to fill a multi-dose medicament order. Fill patterns may correspond to a characteristic of medicaments, such as "take with water" medicaments being packaged together, and "take on an empty stomach" medicaments being packaged together. Fill patterns may be based on date, day, weeks, time period, volume, size of medicaments, user preferences, other characteristics, or combinations thereof. Examples of systems and methods for determining fill patterns may be found, for instance, in U.S. patent application Ser. No. 12/187,218 entitled "Method and System for Determining a Volume-Based Fill Pattern of a Multi-Dose Medicament Container," and in U.S. patent application Ser. No. 12/102,570 entitled "Method and System for Translating a Text Field Associated with a Prescription to a Fill Pattern for a Multi-Dose Medicament Container." Other fill patterns of multi-dose containers are also possible. The disclosure of the present application may also operate in accordance with these and other systems, entities, and methods for determining fill patterns.

Methods and systems for filling multi-dose medicament containers are also known in the art. For example, U.S. patent application Ser. No. 12/130,619 entitled "Multi-Dose Filling Machine," U.S. patent application Ser. No. 12/130,140 entitled "Method of Loading a Multi-Dose Blister Card Using Intermediate Blister Cards," and U.S. patent application Ser. No. 12/130,400 entitled "Method of Loading a Multi-Dose Blister Card Using a Transfer Fixture" disclose systems, or filling entities, for filling a multi-dose blister pack by using a press and one or more transfer fixtures. Said systems may use intermediate containers containing single doses of prescribed medications to transfer pills into multi-dose blister packs. Other filling entities and methods for multi-dose medicament containers are also known in the art. A filling entity may be a mechanical system that is entirely automated by a computer network, it may be an entirely manual system with one or more human beings performing the filling of the prescriptions, or it may be some combination of automated and manual. The disclosure of the present application may also operate in accordance with these and other systems, entities, and methods for filling multi-dose medicament containers.

Figure 1:
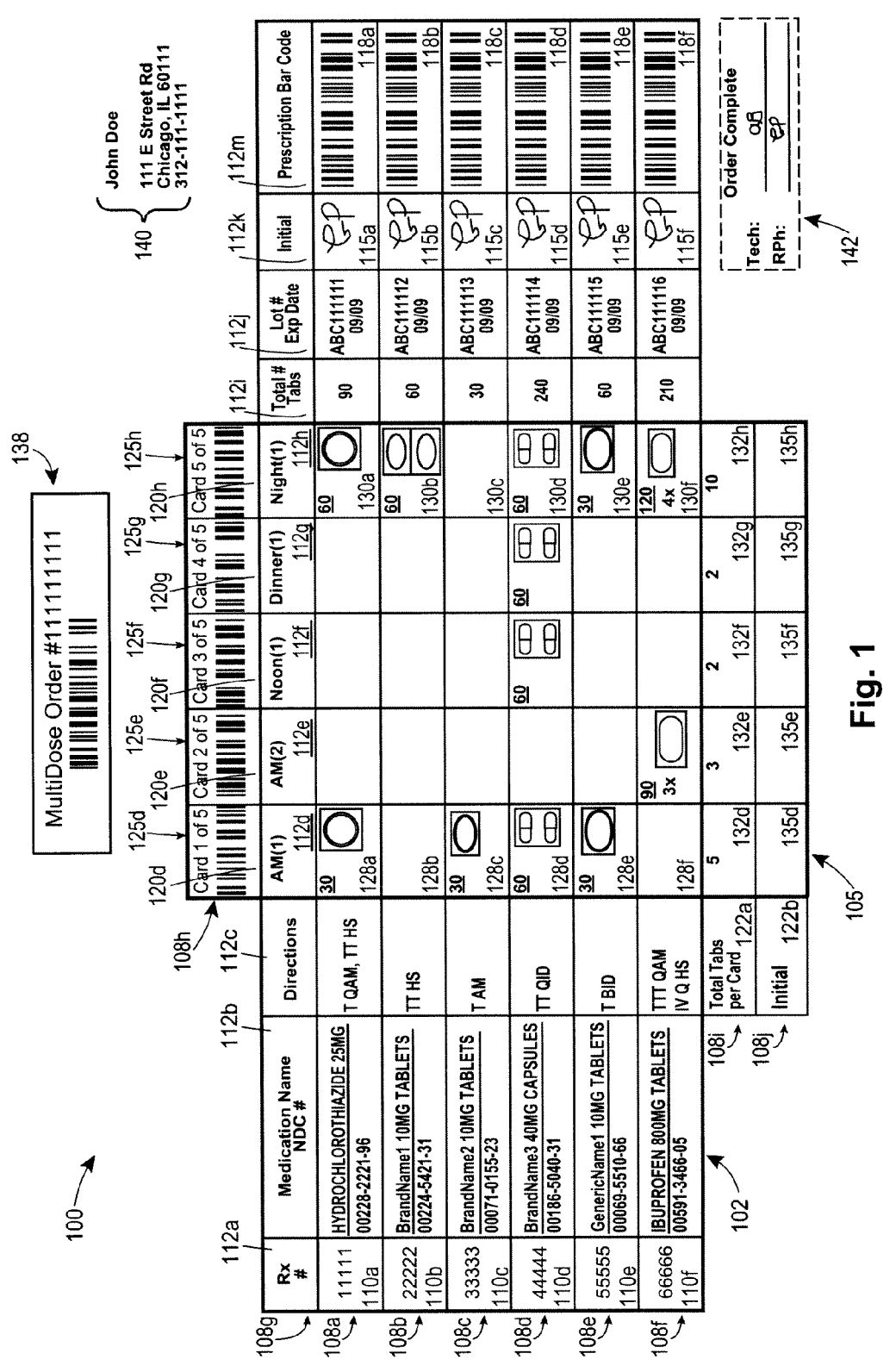

FIG. 1 is an embodiment of manifest 100 of a multi-dose medicament order. The manifest 100 may serve as a type of map or "recipe" for a set of prescriptions and a set of containers required to fill a multi-dose medicament order for a patient. The manifest 100 may be a representation of at least two intersecting matrices, including a prescription matrix 102 and a container matrix 105, and may use a printed and/or electronic format. The prescription matrix 102 may contain information regarding each individual prescription of the multi-dose medicament order, and the container matrix 105 may contain information regarding each individual container of the multi-dose medicament order, as discussed in detail below.

While FIG. 1 illustrates an embodiment of manifest 100 used in accordance with a multi-dose blister pack, this is merely one possible example. Other embodiments of manifest 100 may operate in accordance with other types of multi-dose containers, such as multi-dose rolls of pouches and other multi-dose packaging formats.

In the embodiment illustrated in FIG. 1, the prescription matrix 102 may have a number of rows 108a-108f corresponding to each individual prescription 110a-110f of the multi-dose medicament order. Although six prescriptions 110a-110f are shown in the embodiment of manifest 100, this is merely illustrative. Prescription matrix 102 may have a row corresponding to every individual prescription in the set of prescriptions of the multi-dose medicament order, and thus, the total number of rows of prescription matrix 102 may be equal to the total number of individual prescriptions in the multi-dose medicament order.

Prescription matrix 102 may also have a row 108g with each field 112a-112m of row 108g containing a label for a prescription attribute. The prescription attributes identified by fields 112a-112m of row 108g may correspond to a number of columns of prescription matrix 102. An exemplary set of prescription attributes illustrated in the embodiment of manifest 100 includes an Rx number 112a, a medication or prescription identifier in a textual format or a code format such as an NDC (National Drug Code) 112b, dosing regime instructions for the individual prescription 112c, a total number of units of an individual prescription 112i, lot number and expiration date 112j and/or any legally required information. Attributes 112a-112c, 112i-112j are only exemplary, and are not all required to be in prescription matrix 102. Other prescription attributes (not shown) may be possible, and may have corresponding columns (not shown) on the prescription matrix 102.

Additionally, prescription matrix 102 may have a column corresponding to each individual container of the multi-dose medicament order. In the embodiment illustrated by FIG. 1, each container is shown as a multi-dose blister container, but other types of multi-dose containers may also be used. A field 112d-112h of row 108g in prescription matrix 102 may contain a label corresponding to a dosing regime for each container or container. In the embodiment of manifest 100 in FIG. 1, each of the containers of the multi-dose medicament order corresponds to a relative time of ingestion as indicated by a dosing regime. Two of the containers of the multi-dose medicament order are mapped to contain medicaments to be ingested in the morning as indicated by dosing regime labels "AM(1)" (reference 112d) and "AM(2)" (reference 112e), respectively. Another container is mapped to contain medicaments for ingestion at "noon" (reference 112f). A fourth container corresponds to a container mapped to contain medicaments for ingestion at "dinner" (reference 112g), and a fifth container corresponds to a container mapped to contain medicaments for ingestion at "night" (reference 112h). Of course, as previously discussed, other different configurations of the set of containers for the multi-dose medicament order are also possible, such as containers distinguished by specific times of day, weeks, months, dates, characteristics of medicaments (e.g., color, take with food or take on empty stomach), or even by user selection. Dosing regime labels 112*d*-112*h* may be adjusted to indicate the corresponding dosing regime configuration.

Prescription matrix 102 may have a column (illustrated in FIG. 1 by label 112*k* and fields 115*a*-115*f*) in which a pharmaceutical professional may indicate manual and/or electronic approval for each individual prescription 110*a*-110*f*. In the illustration of FIG. 1, for example, the pharmaceutical professional has indicated approval of each individual prescription 110*a*-110*f* by initialing each field 115*a*-115*f*. Prescription matrix 102 may have a column (depicted in FIG. 1 by label 112*m* and fields 118*a*-118*f*) to provide a machine-readable identifier 118*a*-118*f* for each individual prescription 110*a*-110*f*. The machine-readable identifiers 118*a*-118*f* are depicted in FIG. 1 as bar codes, but other forms of machine-readable identifiers may be possible and may be used in accordance with the instant disclosure. In some embodiments, the column depicted by label 112*k* and fields 115*a*-115*f* and/or the column depicted by label 112*m* and fields 118*a*-118*f* may be optional.

Turning now to the description of container matrix 105, container matrix 105 may have a row 108*h* with each field 120*d*-120*h* of row 108*h* containing a label corresponding to each individual container of the set of containers in the multi-dose medicament order. Container matrix 105 may also have a row corresponding to each individual prescription of the set of prescriptions in the multi-dose medicament order, a row 108*i* indicating a total number of units of medicament per container, and a row 108*j* for use by a pharmaceutical professional to indicate approval (manually or electronically) for each individual container. In some embodiments, row 108*i* and row 108*j* may be optional.

The number of fields in each row of the container matrix 105 may be equal to the total number of containers in the set of containers for the multi-dose medicament order. In the example illustrated by FIG. 1, five containers are depicted, however, any number of containers specified by a multi-dose medicament order may be supported by manifest 100. Rows 108*i* and 108*j* may each have fields 122*a* and 122*b*, respectively, that may be used to contain descriptive labels. In the illustrated embodiment of manifest 100, the rows of container matrix 105 are subsets of rows 108*a*-108*f* of prescription matrix 102, while rows 108*h*-108*j* of container matrix 105 do not intersect with prescription matrix 102.

The container labels 120*d*-120*h* of row 108*h* may contain an alphanumeric identification of each container, and they may also contain a machine-readable identifier for each container. The machine-readable container identifier for each individual container is depicted in FIG. 1 as a bar code, but other types of machine-readable identification may be possible and may be used in accordance with the instant disclosure.

Container matrix 105 may have a column 125*d*-125*h* corresponding to each individual container of the set of containers in the multi-dose medicament order. Each of columns 125*d*-125*h* may contain a field for each individual prescription of the multi-dose medicament order. For example, Container 1 of 5 (120*d*) contains a field 128*a*-128*f* for each prescription 110*a*-110*f*, Container 5 of 5 (120*h*) contains a field 130*a*-130*f* for each prescription 110*a*-110*f*, and so on. Each column 125*d*-125*h* of container matrix 105 may also contain an indication of a total number of units of medicaments mapped to be packaged in the container (132*d*-132*h*), and a field for indicating container approval by a pharmaceutical professional (135*d*-135*h*). In the illustrated embodiment of manifest 100, the columns of prescription matrix 102 are shown as a subset of the columns of container matrix 105 (125*d*-125*h*).

At each field where prescription matrix 102 and container matrix 105 intersect, the manifest 100 may provide an indication of a number of units of the medicament designated by the given individual prescription corresponding to the field that are mapped to be packaged into the given individual container corresponding to the field. For example, Container 1 of 5 (120*d*) is mapped by the manifest 100 to be packaged containing one unit of prescription 110*a* (128*a*), one unit of prescription 110*c* (128*c*), two units of prescription 110*d* (128*d*), and one unit of prescription 110*e* (128*e*). No units of prescriptions 110*b* and 110*f* are mapped to be packaged into Container 1 of 5 (120*d*). Container 5 of 5 (120*h*) is mapped to be packaged containing one unit of prescription 110*a* (130*a*), two units of prescription 110*b* (130*b*), two units of prescription 110*d* (130*d*), one unit of prescription 110*e* (130*e*), four units of prescription 110*f* (130*f*), and no units of prescription 110*c*. The indications of the number of medicaments may be pictorial representations (for instance, as in references 128*c*-128*e*), may be an alphanumeric and a pictorial representation (as, for example, in reference 130*f*), or may be only an alphanumeric representation (not shown).

In one embodiment of manifest 100, dosing regimes may be visually differentiated. For example, in the embodiment of FIG. 1, Container 1 of 5 (125*d*) and Container 2 of 5 (125*e*) both correspond to a dosing regime of "AM" (112*d*, 112*e*). Thus, columns 125*d* and 125*e* are visually differentiated by printing their background in a specific color corresponding to "AM" (112*d*, 112*e*). Container 3 of 5 (120*f*) corresponds to a dosing regime of "Noon" (112*f*) and may be visually differentiated by printing the background of its corresponding column (125*f*) in a different color corresponding to "Noon." Similarly, the backgrounds of columns 125*g* and 125*h* may be visually differentiated by printing their respective backgrounds in other different colors to distinguish their respective dosing regimes (112*g*, 112*h*).

Of course, background color is only one embodiment of visual differentiation between dosing regimes. Other differentiations may be used, for instance, one or more foreground or text colors, font differences, size differences, other types of differentiations or combinations thereof. In the example of a manifest on a screen display, an embodiment of a visual differentiation may even be dynamic (e.g., blinking or flashing) or may be differentiated in response to a user action, such as graying-out columns corresponding to a similar dosing regime that are on-blur, and displaying columns corresponding to a similar dosing regime at full strength that are on-focus.

The manifest 100 may include other information. For example, in one embodiment, an identification of the multi-dose medicament order 138 may be included. The order identification 138 may have an alphanumeric identification, a machine-readable identification, and/or some other form of identification. The machine-readable order identifier 138 for the set of containers is depicted in FIG. 1 as a bar code, but other types of machine-readable identifiers may be possible and may be used in accordance with the instant disclosure.

The manifest 100 may also include patient information 140, including name, address, legally required information, and other information. The manifest 100 may include an order approval field 142 for one or more pharmaceutical professionals to indicate approval (manually or electronically) of the multi-dose medicament order. In the illustration of FIG. 1, both a pharmaceutical technician and a registered pharmacist have initialed their respective approvals in order approval field 142.

Manifest 100 may extend to multiple pages or screens, such as when there are many prescriptions in a single multi-dose medicament order, or when a user requests a manifest to be displayed in a larger format. If manifest 100 extends across multiple pages or screens, order approval field 142 may only appear on one of the multiple pages, or may appear on a cover or a summary page or screen for the order (not shown).

The machine-readable order identifier 138, machine-readable container identifiers 120d-120h, and machine-readable prescription identifiers 118a-118f may be inter-related. For example, machine-readable container identifiers 120d-120h may be derivable from a corresponding machine-readable order identifier 138 by adding or subtracting one or more digits, or by some other algorithm. In another example, if the machine-readable identifier uses a graphical format, a graphical overlay, addition, subtraction or other algorithm may be used. Derivations may be dependent on the particular machine-readable format of the identifiers.

Additionally or alternatively, prescription identifiers 118a-118f may be derivable in a similar fashion from the order identifier 138. Container identifiers 120d-120h may be associated with prescriptions mapped to the container. For example, machine-readable container identifier 120d may be associated with machine-readable prescription identifiers 118a, 118c, 118d, and 118e as each of their corresponding prescriptions 110a, 110c, 110d and 110e have at least one unit of medicament that is mapped to be packaged into Container 1 of 5 (128a, 128c-128e). In an exemplary embodiment, the derivations and associations used between all three types of machine-readable identifiers 138, 120d-120h and 118a-118f for a single manifest 100 may be related.

FIG. 2 illustrates an exemplary embodiment for a method 200 of creating a manifest for a multi-dose medicament order using multi-dose containers. Method 200 may be used, for example, to create embodiments of manifest 100 depicted in FIG. 1.

At the start (block 202) of method 200, multi-dose medicament order information may be obtained from a database (block 205). Order information may include an order identifier such as an order number and/or machine-readable code. The order identification may also include, for example, an identification of the issuing entity such as a pharmacy name, telephone number, address and website, a date of fill for the order, patient name and contact information, and other such data.

At block 208, prescription information for each prescription in the multi-dose medicament order may be automatically obtained. Prescription information may include an Rx number, an identification of the medicaments identified in the prescription (either a textual name, number such as an NDC, or both), a patient identification, dosing regime and instructions, any legally required information such as lot number and expiration date or other legally required information, to name a few. In fact, prescription information may include any of the set of prescription attributes as previously discussed with respect to references 112a-112c and 112i-112m of FIG. 1.

In one embodiment, prescription information may be obtained 208 by a pharmaceutical professional entering the information. The pharmaceutical professional may enter the information manually or electronically. For instance, the pharmaceutical professional may write in the contents of fields onto a manifest in a printed format, or the pharmaceutical may enter contents of the fields via a user interface of a computing device for a manifest in an electronic format. In other embodiments, prescription information may be obtained by receiving the prescription information electronically, such as via a network link. In yet other embodiments, prescription information may be obtained by accessing one or more databases. Prescription information may also be obtained by some combination of the above, or by some other mechanism or method.

At block 210 of method 200, container information for each container of the multi-dose medicament order may be obtained. Container information may include a total number of containers required to fill the order, and an identifier (alphanumeric and/or machine-readable code) for each of the individual containers of the multi-dose medicament order. Container information may be obtained in a fashion similar to obtaining prescription information, such as via input by a pharmaceutical professional, receiving the container information via a network link, by accessing one or more databases, some combination of the above, or by some other method or mechanism of obtaining container information. Container information and prescription information may be obtained (208, 210) via same or different mechanisms or methods.

At block 212, a fill pattern for the multi-dose medicament order may be obtained. A fill pattern, as previously discussed, is a mapping of pills or medicaments from one or more prescriptions of a patient into one or more receptacles of one or more multi-dose medicament containers. A fill pattern may be obtained via methods and/or mechanisms similar to those for obtaining prescription information 208 and for obtaining container information 210, such as via input by a pharmaceutical professional; receiving the fill pattern from a computing entity, either locally or via a network link; by accessing one or more databases; by direct calculation or determination; some combination of the above; or by some other embodiment of obtaining the fill pattern. The fill pattern may be obtained via the same or different mechanisms or methods used for obtaining prescription information and/or obtaining container information, as discussed with reference to blocks 208 and 210.

Next, at block 215, the manifest for the multi-dose medicament order may be generated, using some or all of the obtained order information, prescription information, container information, and fill pattern. A prescription matrix may be generated, such as prescription matrix 102 of manifest 100, and each field or entry of the prescription matrix may be filled in with obtained prescription information. A container matrix may be generated, such as container matrix 105 of manifest 100, and each field or entry of the container matrix may be filled in with container information. The obtained fill pattern may be used to fill in, generally speaking, the contents of the fields at the intersection of the prescription and container matrices. In FIG. 1, for example, the intersection of prescription matrix 102 and container matrix 105 is a sub-matrix bounded vertically by fields 128a-130a and 128f-130f, and bounded horizontally by fields 128a-128f and 130a-130f. Each intersecting entry or field may indicate the number of units of medicaments for each individual prescription mapped by the fill pattern to be packaged into each individual container. The obtained fill pattern may also be used to fill in the fields associated with the dosing regimes (e.g., references 112d-112h of manifest 100) and to provide any desired visual differentiation, such as, for example, different background colors for columns 125d-125h on manifest 100.

At block 218 of method 200, the generated manifest may be displayed. The manifest may be displayed, for example, on a user interface of a computing entity. In another embodiment, the manifest may be sent to a different computing entity for display and/or storage at the different computing entity.

The manifest may be displayed by sending it to a printer or printing entity to produce a hard copy. In some embodiments, multiple displays of the manifest may be possible, such as sending the manifest to more than one local or remote user interface as well as printing a hard copy. In some embodiments, a portion of a manifest may be selected to be displayed, such as displaying only the container matrix 105, displaying selected prescription rows 108a-108f, or displaying approval fields 115a-115f, 142. Finally, at step 220, method 200 may end.

Figure 3:
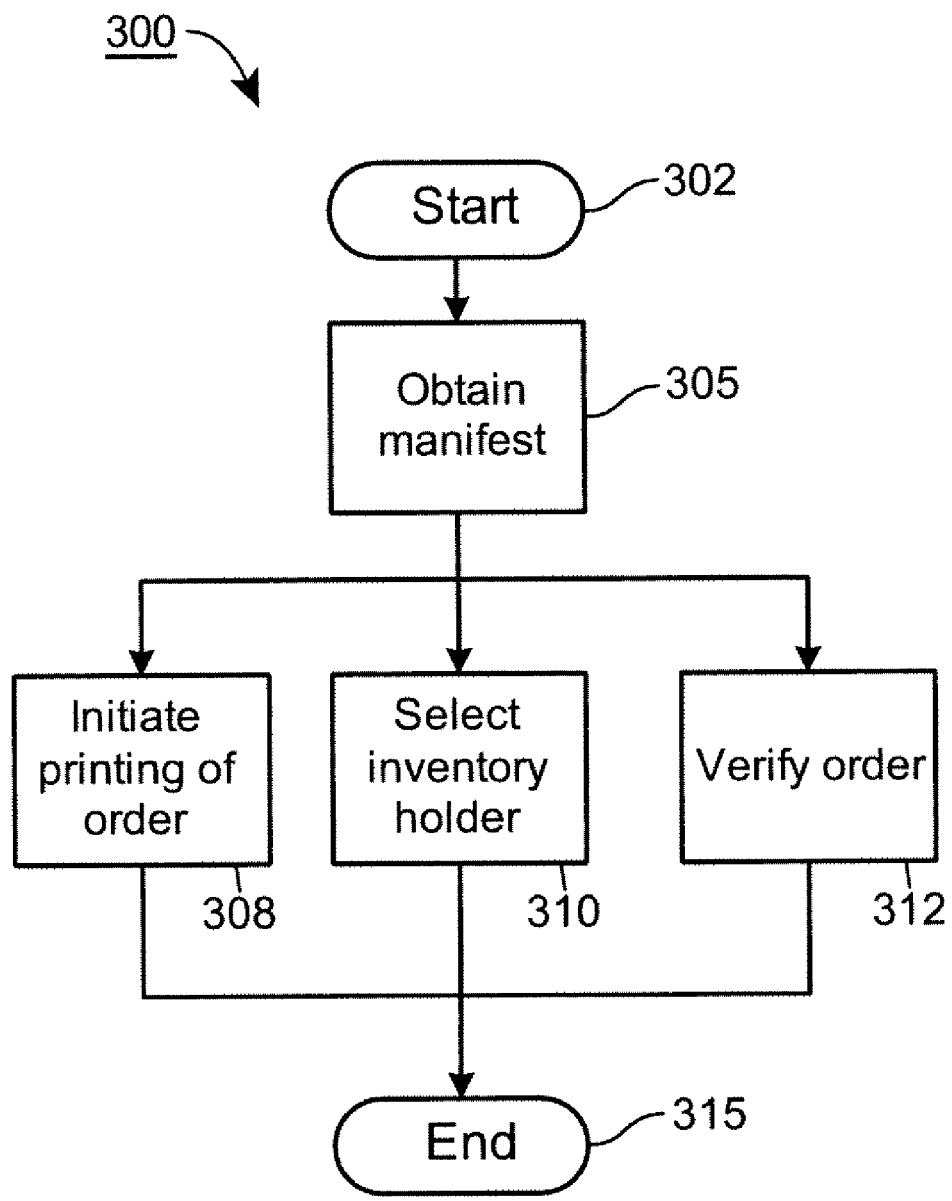
FIG. 3 illustrates an embodiment of a method of using a manifest to fill a multi-dose medicament order.

FIG. 3 illustrates an embodiment of a method 300 of using a manifest to fill a multi-dose medicament order. Method 300 may be used, for example, with embodiments of manifest 100 depicted in FIG. 1, and/or manifests created by embodiments of method 200 of FIG. 2. Method 300 of using a manifest to fill a multi-dose medicament order provides many significant benefits. The manifest allows for a single representation of the multi-dose medicament order to be used by one or multiple people, processes, computing entities, and/or machines while filling the multi-dose medicament order. Not only does the manifest serve as a single "recipe container" or "roadmap" for the filling of the order, but it also may provide a status to the filling process via the approval fields for prescriptions, containers and the order itself. For instance, a quick glance at the approval fields may provide an indication of which step the multi-dose medicament order is at during a fill process. The benefits will become evident during the discussion of method 300 below.

At the start (block 302) of method 300, a manifest for the multi-dose medicament order may be obtained (block 305). The manifest may be of a printed or an electronic format, and may be obtained manually or electronically. In some embodiments, such as when used by high-speed automatic filling entities, the manifest may be entirely represented in software and not displayed in a visual format. The obtained manifest may then be used to perform at least one step for filling the multi-dose medicament order, as represented by blocks 308, 310, and 312. Blocks 308, 310, and 312 are merely an illustrative set of possible steps of filling the multi-dose medicament order that may use the obtained manifest, and are not meant to be a comprehensive set. Other steps used during the filling of a multi-dose medicament order operate in conjunction with method 300.

In some embodiments of method 300, the obtained manifest may be used to perforin only one step in the process of filling a multi-dose medicament order. In other embodiments of method 300, more than one step may use the obtained manifest. In yet other embodiments, all steps performed in the filling of a multi-dose medicament may use a single manifest.

Turning now to individual discussions of possible steps of filling a multi-dose medicament order using a single manifest, the obtained manifest may be used to initiate the printing of portions of the multi-dose manifest order 308. For a multi-dose medicament order, various labels, forms, and accompanying sheets may be required or desired to be printed. Examples of these may include dosing regime and/or instructions, evidence of registered pharmacist approval, warnings and precautions, prescription labels, labels with legally required content, etc. By using a single manifest, printing content may be centralized in one single representation of the order, and may be accessed, in the example of one embodiment, by scanning or reading the machine-readable order identifier. As the container identifiers and prescription identifiers may be derived from the order identifier, a simple, one-step scan of the machine-readable order identifier may provide immediate access to all of the necessary print content.

Thus, with method 300 at block 308, printing content is not required to be obtained from multiple, disparate sources. For example, without a manifest, prescription information may be required to be collected from a first database. Patient information may be required to be collected from a different database, and pharmacist approvals may be required to be collected and stored at yet a different location. These different locations may even be remote and thus require additional steps and administration for their access. By providing a single manifest, however, printing content may be easily consolidated and available in one representation. Multiple database accesses may not be required to be accessed. Multiple connections from multiple databases and/or computing entities to a printing entity may not be required. Time of access, ease of administration, and simplicity of computing entity to printing entity connections may be optimized.

In block 310, the obtained manifest may be used during the step of selecting at least one medicament inventory holder during a fill of a multi-dose medicament order 310. Selecting at least one medicament inventory holder may also be referred to as "picking." For each individual container of a multi-dose medicament order, the various mapped medicaments of the corresponding prescriptions may need to be selected or picked from inventory to be correctly packaged (both in content and in number) into each individual container. For a given individual container, the picking entity (be it an entity that is manual, automated, or some combination of the two) may consult the column of the manifest corresponding to the given individual container. The number of medicaments of each individual prescription required to be selected from inventory for the given individual container may be indicated in the corresponding field of the column and may be used by the picking entity.

One method of picking as known in the art may be a manual "loose" pick method, where a person manually selects an inventory container holding a loose supply of a specific medicament mapped to be packaged into a receptacle an individual container of the multi-dose medicament order, and counts out the required number of units of the specific medicament from the inventory container.

A variation on the manual "loose" pick method may include an automatic or semi-automatic method that counts out the required number of units of a specific medicament from a loose inventory supply, such as a vat or a bin.

Another method of picking may use intermediate inventory containers, where a person or automated process may select/pick an intermediate inventory container for use in the fill of the multi-dose medicament order. One example of intermediate inventory containers may be the use of intermediate inventory containers to fill multi-dose blister packs. In this example, a configuration of blister cells on an inter mediate inventory container may directly map to the blister cell configuration of an individual pack or container of the multi-dose medicament order. Each blister of the intermediate inventory container may contain one unit of a particular medicament. In this case, multiple intermediate inventory containers corresponding to the number and/or types of multiple medicaments to be packaged into an individual container may be manually or automatically picked. The medicaments from each multiple intermediate inventory container may be "pushed through" the intermediate inventory container into the individual container to fill the individual container with the desired combination of medicaments. Of course, the use of intermediate inventory containers is not limited to filling only multi-dose blister packs, but may apply to filling other forms of multi-dose medicament containers as well.

A variation on picking intermediate inventory containers for filling an individual container of the multi-dose medicament order may include picking a pre-filled inventory container. A pre-filled inventory container may include receptacles filled with a frequently prescribed dose of a number of units of a medicament. For example, if the dosing regime of medicament A is frequently prescribed as requiring ingestion of two units of medicament A at a time, a pre-filled inventory container may have receptacles each with two units of medicament A. Pre-filled inventory containers may thus save the total number of picks required for a multi-dose medicament order, as well as save space required to hold the inventory.

More than one different picking method may be used to fill a single multi-dose medicament order. Block 310 of method 300 may operate in conjunction with one or more of the aforementioned picking methods and/or inventory holding containers. In fact, block 310 of method 300 may operate in conjunction with any other known picking methods and inventory holding containers.

At block 312, the manifest may be used to verify the multi-dose medicament order. The verification may be performed by a manual verification entity, an automatic verification entity, or some combination of the two. Method 300 may operate in conjunction with any type of verification entity and/or method used in the filling of a multi-dose medicament order, such as in U.S. patent application Ser. No. 12/130,489 entitled "Method and System for Verification of Product Transfer from an Intermediate Loading Cartridge to a Multi-Container Blister Pack" and U.S. patent application Ser. No. 12/130,575 entitled "Method and System for Verification of Contents of a Multi-Cell, Multi-Product Blister Pack."

Several levels of verification are conveniently provided by the manifest. For example, a filled container may be verified for correctness by checking the packaged contents of the filled container against a column of the manifest corresponding to the filled container. Identifications (in a pictorial, textual and/or other format) and quantities of units of each individual prescription mapped to be packaged into the filled container as well as a total number of units mapped for the filled container may be easily seen. Upon correct verification, an approval from a pharmaceutical professional may be obtained, for instance, in a container approval field corresponding to the filled container (e.g., references 135$d$-135$h$ of manifest 100).

Individual prescriptions may also be verified using a manifest. For example, each filled container of the multi-dose medicament order may be verified for correctness by checking the packaged contents of each filled container against a row of the manifest corresponding to the individual prescription. Identifications (in a pictorial, textual and/or other format) and quantities of units for the individual prescription mapped to be packaged into each filled container may be easily seen. Upon correct verification, an approval from a pharmaceutical professional may be obtained, for instance, in a prescription approval field corresponding to the individual prescription (e.g., references 115$a$-115$f$ if manifest 100).

The complete, filled, multi-dose medicament order may also be verified by using a manifest. For example, each filled container may be verified, and/or each individual prescription may be verified. Upon correct verification of all filled containers and/or all individual prescriptions, an approval from a pharmaceutical professional may be obtained, for instance, in an order approval field such as reference 142 of manifest 100.

Verification at any level (e.g., at a container, prescription and/or order level) may be performed manually, such as having a person check a filled container, prescription and/or order against the manifest. Verification at any level may be performed automatically, such as by using a computer to scan contents of the filled container, prescription and/or order and to check the scanned contents against the manifest. In some embodiments, verification may be performed with a combination of manual and automatic verification methods.

Note that approval fields (row 108$j$, column 112$k$ and fields 115$a$-115$f$, and reference 142) may also be used for record keeping and for tracking status of the fill of the multi-dose medicament order. Approval fields having indication of approvals (e.g., initials, signatures, and the like) not only may signify that an entity has been verified, but may provide a record of the identity of the approver, and also show that the particular fill step has been performed. In some embodiments, an approval field may also include other pertinent tracking information, such as a time stamp or a location identifier. A person or entity may consult the manifest of a multi-dose medicament order at any time during its fill process and easily follow the status of the fill. Finally, at block 320, method 300 may end.

Figure 4:
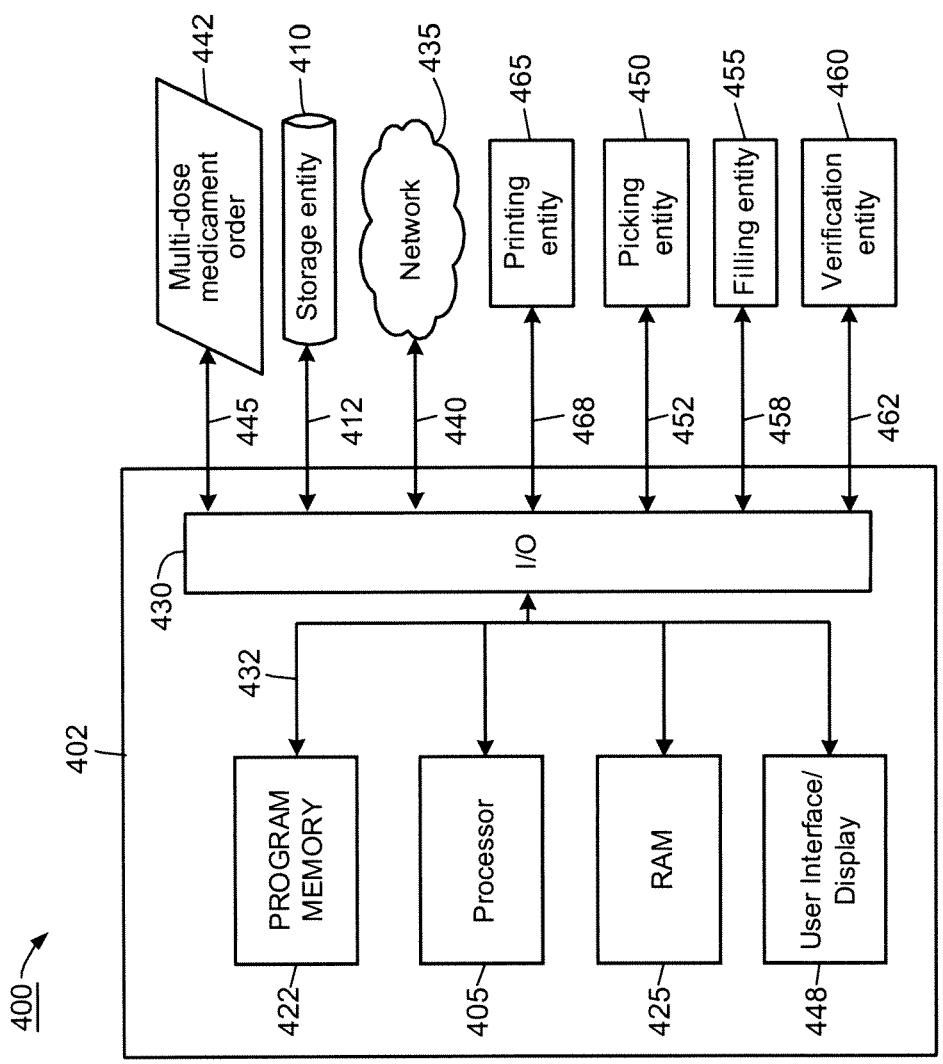
FIG. 4 shows an exemplary embodiment of a system for performing the methods of the present disclosure.

FIG. 4 shows an exemplary embodiment of a system 400 for performing the methods of this disclosure. System 400 may operate in accordance with embodiments of methods 200 and 300 of this disclosure, and in conjunction with embodiments of manifest 100 of FIG. 1.

For the sake of illustration, a simplified block diagram of a computer 402 is used to illustrate the principles of the instant disclosure. However, such principles apply equally to other electronic devices, including, but not limited to, cellular telephones, personal digital assistants, media players, appliances, gaming systems, entertainment systems, set top boxes, and automotive dashboard electronics, to name a few. The computer 402 may have a processor 405 that is operatively connected to a database or storage entity 410 via a link 412. Link 412 may be as simple as a memory access function, or it may be a wired, wireless, or multi-stage connection through a network. Many types of links are known in the art of networking and are possible. Alternatively, the storage entity 410 may be contained in the same entity as the computer 402. It should be noted that, while not shown, additional databases may be linked to the computer 402 in a known manner. The storage entity 410 may include any data that may be relevant to creating and using a manifest to fill a multi-dose medicament order, such as order information, prescription information, container information, and fill patterns.

The computer 402 may include a processor 405 (may be called a microcontroller or a microprocessor) for executing computer executable instructions, a program memory 422 for permanently storing data related to the computer executable instructions, a random-access memory (RAM) 425 for temporarily storing data related to the computer executable instructions, and an input/output (I/O) circuit 430, all of which may be interconnected via an address/data bus 432. It should be appreciated that although only one processor 405 is shown, the computer 402 may include multiple processors 405. Similarly, the memory of the computer 402 may include multiple RAMs 425 and multiple program memories 422. Although the I/O circuit 430 is shown as a single block, it should be appreciated that the I/O circuit 430 may include a number of different types of I/O circuits. The RAM(s) 425 and program memories 422 may be implemented as semiconductor memories, magnetically readable memories, and/or optically readable memories, for example. The computer 402 may also be operatively connected to a network 435 via a link 440. Similar to link 412, the form of link 440 may take any form known in the art of networking.

Computer 402 may contain computer-executable instructions for performing embodiments of method 200 for creating a manifest, and of method 300 for using a manifest in filling a multi-dose medicament order. Alternatively or additionally, computer 402 may store embodiments of manifest 100.

The computer 402 may receive multi-dose medicament order information 442 over a link 445. Multi-dose medicament order information may include, for instance, order information, prescription information, container information, and/or filling patterns. Link 445 may be the same entity as network link 440 or database link 412, or it may be a separate entity. Link 445 may be an operator/user interface, or it may be a local or remote network connection to a server, website, other computer, or a different database. The computer 402 may receive multi-dose medicament order information 442 from a plurality of sources, for example, when a single computer 402 receives prescription information 442 for multiple prescriptions from multiple medical entities such as doctors' offices, hospitals, and the like, and receives a fill pattern from a computing entity at a fill site. In this case, multiple links 445 are possible. Multi-dose medicament order information 442 may also be partially or totally entered via user input, such as via user interface 448.

The computer 402 may be operatively connected to a picking entity 450. Picking entity 450 may pick or select medicament inventory holders to use in the filling of the multi-dose medicament order. Picking entity 450 may select, for instance, from a loose supply of medicaments in a container, from an intermediate inventory container, a pre-filled inventory container, or other inventory holding containers. A picking entity 450 may be manual, semi-automatic, automatic, or some combination of the above. In the cases of semi-automatic and automatic, picking entity 450 may be connected to computer 402 via a link 452. Multiple links 452 to multiple picking entities 450 may be possible, for instance, if separate picking entities exist for different types of inventory holding containers. Link 452 may be the same link as links 412, 440 or 445, or it may be a separate link. Link 452 may also be a local connection or a remote connection through network 435.

The computer 402 may also be operatively connected to a filling entity 455 via a link 458 for communicating a fill pattern for the multi-dose medicament order. Filling entity 455 may fill and package medications into one or more multi-dose medicament containers according to the fill pattern received from computer 402. Filling entities 455 may be automatic processes or systems, they may be manual, semi-automatic, or some combination of the above. Filling entities may be high or low speed. Multiple links 458 to multiple filling entities 455 may be possible, for instance, if separate filling entities exist for different types of medicament containers. Link 458 may be the same link as links 412, 440, 445, or 452 or it may be a separate link. Link 458 may also be a local connection or a remote connection through network 435.

The computer 402 may be operatively connected to a verification entity 460 via link 462 for verification of a filled container, a prescription, and/or the multi-dose medicament order itself. Verification entity 460 may be manual, such as a pharmaceutical professional. Verification entity 460 may be automatic, such as an entity that has a scanning mechanism to automatically detect the identity of medicaments from, for example, size, shape, color, or code, to name a few. Verification entity 460 may be semi-automatic, for instance, when a remote or local pharmaceutical professional views a generated image of a filled multi-dose medicament package. In other embodiments, verification entity 460 may be some combination of manual, automatic, and/or semi-automatic. Multiple links 462 to multiple verification entities 460 may be possible, for instance, if container level verification is done automatically but order level verification is done manually. Link 462 may be the same link as links 412, 440, 445, 452 or 458 or it may be a separate link. Link 462 may also be a local connection or a remote connection through network 435.

The user interface or display 448 may be employed for exhibiting the manifest 100. Any known technology of user interface or display may be used in system 400, including, for example, computer displays, touch-screens, LED screens and the like. Computer 402 may additionally or alternatively display a manifest 100 for a multi-dose medicament order by sending it to a printing entity 465 via link 468, or by sending it to another computer (not shown) via network 435.

Different embodiments of system 400 for using a manifest to fill a multi-dose medicament order may be employed in various filling scenarios. In one embodiment, a store-front pharmacy may have several maintenance prescriptions for a patient who desires them to be packaged into a multi-dose medicament container. In this embodiment, a computer 402 at the store-front pharmacy may already contain prescription and patient information in a database 410. An existing program (not shown) on the computer 402 may generate a fill pattern and the number of containers required for the patient's multi-dose medicament order. The computer 402 may then use an embodiment of method 200 to create a manifest of the patient's order and store the manifest in memory. A pharmacy professional may request to view the manifest via user interface 448, and/or print out a hard copy via printer 465. The pharmaceutical professional may serve as a manual picking entity 450, filling entity 455 and verification entity 460, and use the generated manifest to fill the patient's order. Approvals may be electronically or manually signed and dated, and the manifest may be stored in database 410 for record keeping.

In another embodiment of system 400, a website pharmacy may be a point-of-sale for a multi-dose medicament order. The website server 402 may receive prescription and patient information and preferences for the multi-dose medicament order via a network 435 and link 440. The website server 402 may coordinate various interfaces with other entities to perform steps in filling the order. For instance, the website server 402 may request another computing entity (not shown) in network 435 to determine a fill pattern and a number of containers required for the order. The website server 402 may receive the determined fill pattern and number of containers and create a manifest, for example, by using an embodiment of method 200. The website server may then send the manifest via link 452 to a combination high-speed picking/filling entity (450, 455), perhaps in another physical location where large amounts of inventory may be available (to maximize fill efficiency), or at a location near the patient (to minimize shipping costs or to allow patient pick-up). The combination high-speed picking/filling entity (450, 455) may consult the manifest and automatically pick inventory and fill the containers of the multi-dose medicament order. A visual scanner of the combination high-speed picking/filling entity (450, 455) may scan and send a visual image of the packaged order to a verification entity 460 in yet another location, such as to a registered pharmacist in a remote location. The registered pharmacist 460 may receive the manifest from website server 402, and use it to verify the contents of the packaged order as shown by visual image sent from the combination high-speed picking/filling entity (450,455). The registered pharmacist 460 may then indicate electronic approval on the manifest, and the approved manifest may be stored back at website server 402 (or, perhaps via website server 402 at storage entity 410) for record-keeping. The manifest may also track the identity of the combination high-speed picking/filling entity (450,455) in the approval field. Website server 402 may then inform in the patient that the multi-dose medicament order has been packaged and shipped or is ready for pick-up.

FIGS. 5-10 each illustrate a different embodiment of a manifest, with each different embodiment corresponding to a different multi-dose medicament order having a different combination of intersecting dosing regimes. Each of FIGS. 5-10 may depict a permutation, variation, extension or enhancement of concepts illustrated by the manifest 100 of FIG. 1.

FIG. 5 illustrates an embodiment of a manifest 500 for filling a multi-dose medicament order. Similar to the embodiment depicted by manifest 100, the embodiment depicted by manifest 500 may support a multi-dose medicament order to be packaged into multi-dose blister containers. (Of course, the manifest 500 may support multi-dose medicament orders to be packaged into multi-dose containers other than multi-dose blister containers or packs.) Manifest 500 may be used, for example, when a fill pattern for the multi-dose medicament order indicates that the assortment of medicaments to be co-packaged into a single receptacle is the same for a given relative time of ingestion for every day of a week, and for every week of the multi-dose medicament order. For instance, manifest 500 may be used when a fill pattern for the multi-dose medicament order indicates that an assortment of co-packaged medicaments to be ingested on "Monday Night" of Week 1 is the same assortment to be ingested at "Night" on each of the other days of Week 1, and, additionally, is also the same assortment to be ingested at "Night" for all days (e.g., "Sunday Night," "Monday Night," ..., "Saturday Night") of Weeks 2, 3, and 4 of the multi-dose medicament order.

Manifest 500 thus may support a fill pattern with each individual container of the multi-dose medicament order corresponding to a given week. Within each individual weekly container, different relative times of ingestion may be indicated.

Each individual weekly container may be represented on the manifest 500, for example, by a corresponding machine-readable container identifier 502a-502d. Each individual weekly container 502a-502d may have a plurality of receptacles, with each individual receptacle mapped to contain a co-packaged assortment of medicaments specific to a combination of a particular day of the week (e.g., "Sunday," "Monday," "Tuesday," etc.) and a specific relative time of ingestion (e.g., "Morning," "Noon," "Evening," "Bedtime," etc.). In one embodiment, each individual weekly container 502a-502d may have thereon a grid of individual receptacles (not shown), with one axis of the grid corresponding to days of the week and the other axis of the grid corresponding to different relative times of ingestion. A specific set of different relative times of ingestion to be included on the grid may be selectable, and may each be differentiated on the grid by color or by some other scheme. For example, for a specific weekly container, a row on the grid corresponding to "Morning" may have a yellow background color, and a different row on the grid corresponding to "Night" may have a purple background color.

In some aspects, the manifest 500 may be similar to the manifest 100 of FIG. 1. For example, the manifest 500 may serve as a type of map or "recipe" for a set of prescriptions and a set of containers needed to fill the multi-dose medicament order for a patient, and may use an electronic format or a printed format. The manifest 500 may include a machine-readable order identifier 505 for the multi-dose medicament order, and may include patient information 508 such as patient name, address, and other patient information. The manifest 500 may also include legally required information, store information, dates of fill, dates corresponding to a weekly identification, prescribing entity identification, and other information. Manifest 500 may contain an order approval field 510 for receiving an indication of approval of the multi-dose medicament order by a technician and/or a registered pharmacist.

Also similar to the manifest 100 of FIG. 1, the manifest 500 may be a representation of at least two intersecting matrices, including a prescription matrix 512 and a container matrix 515. The prescription matrix 512 may generally be similar to the prescription matrix 102 of FIG. 1, such as including a number of rows 518a-518f corresponding to individual prescriptions 520a-520f of the multi-dose medicament order. The total number of rows of prescription matrix 512 may be equal to the total number of individual prescriptions in the multi-dose medicament order.

Prescription matrix 512 may also have a row 518g having entries containing labels for prescription attributes. Each prescription attribute may correspond to a separate column of prescription matrix 512, with each entry of a column corresponding to an individual prescription 520a-520f. Prescription attributes may include attributes similar to those previously discussed for manifest 100, including, for example, an Rx number, a medication or prescription identifier in a textual format or a code format such as an NDC (National Drug Code), dosing regime instructions for an individual prescription, a total number of units of the individual prescription, a pictorial representation of the medicament of the individual prescription, and legally required information such as lot number, expiration date and/or other legally required information. The set of attributes illustrated in the row 518g of the manifest 500 are exemplary. Not all illustrated prescription attributes are required to be in prescription matrix 512. Other prescription attributes (not shown) may be possible, and may have corresponding columns (not shown) on the prescription matrix 512.

Additionally, the prescription matrix 512 may also contain a column corresponding to a prescription approval field 522 in which a technician, pharmacist, or other phainiaceutical professional may indicate approval for each individual prescription (e.g., electronic or manual, dated or not dated). Prescription matrix may contain a column corresponding to a machine-readable prescription identifier 525, with each entry in the column 525 corresponding to an individual prescription 520a-520f.

The prescription matrix 512 may have columns 528a, 528b, 528c each corresponding to an assortment of medicaments assigned, by the fill pattern, to a given relative time of ingestion and mapped to be packaged into an individual receptacle of the multi-dose medicament container. The assortment of medicaments for a given relative time of ingestion may be represented by a machine-readable assortment identifier, as illustrated in the header of each column 528a-528c. The machine-readable assortment identifiers in the headers of columns 528a-528c and the machine-readable identifiers 502a-502d, 505 and 525 are depicted in FIG. 5 as bar codes, but other forms of machine-readable identifiers are possible and may be used in accordance with the instant disclosure. Similar to machine-readable identifiers of FIG. 1, machine-readable identifiers 502a-502d, 505, 522 and the machine-readable assortment identifiers shown in the headers for columns 528a-528c may be co-derivable.

In the example illustrated by the manifest 500, two of the columns (528a, 528b) may indicate two different assortments of medicaments mapped to be ingested in the morning. For example, column 528a is labeled with "Morning (1)" and column 528b is labeled with "Morning (2)." Another column 528c may indicate a different assortment of medicaments for ingestion at "Night." Of course, instead of relative times of ingestion, other different characteristics may be indicated by of the set of columns 528a-528c in prescription matrix 512, for example, color, ingestion instructions (e.g., take with food, take with water, take on empty stomach, etc.), user selection, etc. Indeed, any set of characteristics may be represented in columns 528a-528c of manifest 500 as long as the assortment of medicaments mapped to be packaged into an individual receptacle for a specific characteristic remains constant for each day of each week in the multi-dose medicament order.

The container matrix 515 may have columns 528a, 528b, 528c each corresponding to an assortment of medicaments assigned, by the fill pattern, to a given relative time of ingestion and mapped to be packaged into an individual receptacle of a multi-dose medicament container. Each relative time of ingestion may be differentiated by a different background color. For example, columns 528a and 528b may have a same color background to signify "Morning," and column 528c may have a different background color to signify "Night." Alternatively or additionally, other differentiation schemes may also be used, such as different foreground or text colors, font sizes, dynamic representations (e.g., blinking or flashing on a screen), and the like. The container matrix 515 may have rows corresponding to each individual prescription 520a-520f. The container matrix 515 may also have an optional row 530 with each entry in the row having an indication of a total number of medicaments to be packaged into an individual receptacle.

At each field where prescription matrix 512 and container matrix 515 intersect, the manifest 500 may provide an indication of a number of units of the medicament designated by the given individual prescription that are mapped to be packaged into an individual receptacle. In the embodiment of manifest 500, each individual prescription may have a pictorial representation of the front (denoted by a label "F" on the pictorial representations) and the back (denoted by "B" on the pictorial representations) of the physical medicament, and the indication of the number of units may be numeric. In other embodiments, the indications of the number of medicaments may use pictorial representations (e.g., four pictorial representations of pill A to indicate four units) and/or alphanumeric representations.

On manifest 500, each individual receptacle corresponding to a "Morning (1)" time of ingestion for each day of each week of the multi-dose medicament order is mapped by the manifest 500 to be packaged with one unit of prescription 520a (532a), one unit of prescription 520c (532c), two units of prescription 520d (532d), and one unit of prescription 520e (532e). No units of prescriptions 520b and 520f are mapped to be packaged into the individual receptacle containing the assortment of medicaments for "Morning (1)" (528a). Each individual receptacle corresponding to a "Morning (2)" time of ingestion for each day of each week of the multi-dose medicament order is mapped by the manifest 500 to be packaged with only three units of prescription 520f (533a). Each individual receptacle corresponding to "Night" (528c) time of ingestion for each day of each week of the multi-dose medicament order is mapped to be packaged containing two units of prescription 520a (534a), two units of prescription 520b (534b), two units of prescription 520d (534d), one unit of prescription 520e (534e), four units of prescription 520f (534f), and no units of prescription 520c. The indications of the number of medicaments shown in each intersecting field of prescription matrix 512 and container matrix 515 may include pictorial and/or alphanumeric representations.

Although FIG. 5 illustrates the manifest 500 as representing weekly containers (502a-502d), other embodiments of the manifest 500 may be possible. For example, instead of weekly containers, each of container references 502a-502d may correspond to a relative time of ingestion (e.g., Morning, Noon, Evening, Night), and each column 528a-528c may correspond to a specific week. In another embodiment, the manifest 500 may not be limited to only four weeks but may include any number of weeks. Other embodiments or combinations of embodiments of the manifest 500 are also possible.

FIGS. 6A and 6B jointly illustrate an embodiment of a manifest 600 for filling a multi-dose medicament order. The manifest 600 may generally be similar to the manifest 500 in that manifest 600 may also support a multi-dose medicament order to be packaged into weekly containers, but the manifest 600 may also support a fill pattern that includes dosing regime differences from week to week. For example, the manifest 600 may be used for a fill pattern including an individual prescription for a medicament that has a varying dosing regime on alternating weeks. Other fill patterns requiring differentiation on a weekly basis may also use embodiments of manifest 600.

The manifest 600 may include multiple instances (e.g., reference 602a of FIG. 6A and reference 602b of FIG. 6B) of prescription matrix and container matrix intersections, with each instance corresponding to a particular week (and accordingly, to a particular individual container) of the multi-dose medicament order. For clarity's sake, the manifest 600 is illustrated using two separate figures, FIGS. 6A and 6B, however it is understood that both instances 602a and 602b are parts of the same manifest 600. FIG. 6A, reference 602a may illustrate an instance of manifest 600 corresponding to Week 1, and FIG. 6B, reference 602b may illustrate an instance of manifest 600 corresponding to Week 2. Additional instances of intersections (not shown) may also be included in manifest 600, for example, instances corresponding to Week 3, Week 4, etc.

Manifest 600 may generally be similar to manifest 500 in its characteristics and attributes, so a detailed description of common features and characteristics shared by manifest 500 and manifest 600 will not be repeated here. Some differences do exist, however, primarily to support the differences in fill patterns. For example, in manifest 600, each machine-readable weekly container identifier 602a, 602b may be associated with a corresponding instance of prescription matrix and container matrix intersection. For instance, the instance 602a corresponding to Week 1 may contain a machine readable-identifier 605a corresponding to Week 1, and the instance 602b corresponding to Week 2 may contain a machine-readable identifier 605b corresponding to Week 2.

Also, manifest 600 may provide indications of differences in the fill pattern from week to week. For instance, manifest 600 may indicate three units of prescription 608 are to be packaged into each daily individual receptacle corresponding to "Morning(2)" of Week 1 (as shown in reference 610a), but only two units of prescription 608 are to be packaged into each daily individual receptacle corresponding to "Morning (2)" of Week 2 (as shown in reference 610b). Also, manifest 600 may indicate four units of prescription 608 are to be packaged into each daily individual receptacle corresponding to "Night" of Week 1 (reference 612a), but only two units of prescription 608 are to be packaged into each daily individual receptacle corresponding to "Night" of Week 2 (reference 612b). In this fashion, the embodiment illustrated by manifest 600 may support a multi-dose medicament order having prescription(s) with dosing regimes that may differ from week to week, where the medicaments of the prescription(s) are to be packaged into individual containers corresponding to a week's worth of medicaments.

Although FIGS. 6A and 6B illustrate the manifest 600 as representing weekly containers (605a, 605b), other embodiments of the manifest 600 may be possible. For example, instead of corresponding to weekly containers, container references 605a and 605b may correspond to relative times of ingestion (e.g., Morning, Noon), and additional cards may be added to the manifest 600 corresponding to other times of ingestion (e.g., Evening, Night). In this example, each container matrix column on 602a and 602b may correspond to a specific week. In another example, the manifest 600 may not be limited to only four weeks but may include any number of weeks. Other embodiments or combinations of embodiments of the manifest 600 are also possible.

Daily variations in the assortment of medicaments mapped to be packaged together into an individual receptacle may be supported by an embodiment of a manifest 700 for a multi-dose medicament order, as illustrated in FIG. 7. The manifest 700 may generally be similar to the manifest 100 of FIG. 1, in that each individual container may correspond to a relative time of ingestion. The manifest 700, however, may allow for daily differences required by dosing regimes. For example, the manifest 700 may be used to support fill patterns where an individual medicament of a multi-dose medicament order is required to be taken every other day, as well as other fill patterns having daily differences in prescription dosing regimes.

Manifest 700 may generally be similar to manifest 100 in its characteristics and attributes, so a detailed description of common features and characteristics shared by manifest 700 and manifest 100 will not be repeated here. Some differences do exist, however, to support the different fill patterns. For example, in the manifest 700, each intersecting entry of prescription matrix 702 and container matrix 705 may provide an indication of a number of units of each individual prescription mapped to be packaged into each individual receptacle of an individual weekly container. This indication may be a pictorial representation, an alphanumeric representation, or a combination of both.

To illustrate this point, consider a container corresponding to a "Morning" time of ingestion, as represented on manifest 700 by column 708. The "Morning" container may include individual receptacles corresponding to all of the days of a month. Each entry of column 708 may contain an indication of a number of units of medicaments to be packaged into each individual receptacle. So, in the example shown by manifest 700, each individual receptacle may be mapped to include one unit of prescription 710a for each day of the month (reference 712a). Each individual receptacle may also be mapped to include no units of prescription 710b (reference 712b) and one unit of prescription 710c (reference 712c). Prescription 710d, however, may be required by its dosing regime (reference 715) to be ingested every other day. Therefore, manifest 700 may indicate, as shown in reference 712d, that only every other individual receptacle of the "Morning" container may be mapped to contain one unit of prescription 710d. Thus, in this scenario, an individual receptacle for Day 1 of the "Morning" container may be mapped by the manifest 700 to be packaged with one unit of each of prescriptions 710a, 710c and 710d. An individual receptacle for Day 2 of the "Morning" container may be mapped by the manifest 700 to be packaged with one unit of each of prescriptions 710a and 710c but no units of prescription 710d. An individual receptacle for Day 3 of the "Morning" container may be mapped by the manifest 700 to be packaged with one unit of each of prescriptions 710a, 710c and 710d, and this mapping pattern may continue for the remaining individual receptacles for the month. In this manner, the embodiment illustrated by manifest 700 may allow for differences at the individual receptacle level.

Additional embodiments of the manifest 700 are also possible. For example, the manifest 700 may not be limited to only a thirty day supply of individual receptacles but may include any number of receptacles corresponding to any size supply. In another embodiment, instead of only two relative times of ingestion, any number of relative times of ingestion may be represented. In yet another embodiment, containers may not be distinguished by relative time of ingestion (i.e., "Morning" and "Night") but may be distinguished by any type of characteristic, such as how the medication is to be ingested (e.g., with food, with water, on an empty stomach, etc.), by user preference, or by some other characteristic. Other embodiments of the manifest 700 are also possible.

Figure 8:

FIG. 8 illustrates an embodiment of a manifest 800 for a multi-dose medicament order supporting a fill pattern where each individual container corresponds to a relative time of ingestion. Manifest 800 may be generally similar to the embodiment illustrated by manifest 700 of FIG. 7, and so a detailed description of common features and characteristics shared by manifest 700 and manifest 800 will not be repeated here. Manifest 800, however, may be used to support fill patterns that have differences in dosing regimes at the weekly, but not daily, level. For example, manifest 800 may be used to support a fill pattern including another medicament with a dosing regime of a daily dose for the first and third weeks and no dose for the second and fourth weeks. Other fill patterns corresponding to intersecting dosing regimes with weekly (but not daily) differences may be supported by manifest 800.

Accordingly, some differences between manifest 700 and manifest 800 may exist to support the different fill patterns. For example, unlike manifest 700, each intersecting entry of prescription matrix 802 and container matrix 805 in manifest 800 may not be required to detail the mapped contents of each individual receptacle. Instead, each intersecting entry of prescription matrix 802 and container matrix 805 may merely illustrate an indication of a number of medicaments for a particular individual prescription 808a-808f mapped to be packaged into each individual receptacle without showing a representation of each individual receptacle itself, as the mapping remains constant for each day of the week.

To illustrate this point, consider prescription 808f shown on manifest 800. A dosing regime 810a of prescription 808f may indicate that three units of prescription 808f are to be ingested in the morning and in the night every day for three weeks, and for the fourth week, no units are to be ingested (references 810b and 810c). Thus, for the "Night" container 815, the manifest 800 may indicate that each individual receptacle corresponding to each day of Weeks 1, 2, and 3 may be mapped to contain two units of prescription 808a, two units of prescription 808b, two units of prescription 808d, one unit of prescription 808e and three units of prescription 808f. For Week 4 of the "Night" container 815, however, each individual receptacle may be mapped to contain the same assortment as in Weeks 1, 2, and 3 but the three units of prescription 808f may be excluded. In this manner, manifest 800 may support prescriptions in a multi-dose medicament order that have weekly (but not daily) dosing regime differences.

Other embodiments of the manifest 800 may be possible. For example, manifest 800 may not be limited to only four weeks or five times of relative ingestion, but may include any number of weeks and any number of times of relative ingestion. In another embodiment, instead of containers corresponding to relative times of ingestion (e.g., Morning (1), Morning (2), Noon, Evening and Night) and subdivided by weeks (Week 1, 2, 3, 4), the manifest 800 may include containers corresponding to weeks and subdivided by relative times of ingestion. Other embodiments or combinations of embodiments of the manifest 800 are also possible.

Figure 9:

FIG. 9 shows an embodiment of a manifest 900 for a multi-dose medicament order where individual containers of the order are apportioned on a weekly basis. Manifest 900 may support a multi-dose medicament order fill pattern including prescriptions with dosing regimes that vary from day to day. Similar to the other previously discussed embodiments, manifest 900 may include a prescription matrix 902 and a container matrix 905. Columns corresponding to each weekly container (908*a*-908*d*) may exist in the intersection of prescription matrix 902 and container matrix 905. Each intersecting entry (e.g., 910*a*-910*d* and other intersecting entries) of prescription matrix 902 and container matrix 905 may provide an indication of a number of units of an individual prescription (e.g., as indicated by one of 912*a*-912*d*) mapped to be packaged into each individual receptacle of a specific container. This indication may be a pictorial representation, an alphanumeric representation, or a combination of both. In this embodiment, within each intersecting entry (e.g., 910*a*, 910*b*, 910*c* or 910*d*), each row may correspond to a relative time of ingestion and each column may correspond to a day of the week (e.g., "Sunday," "Monday," . . . , "Saturday").

Note that within each intersecting entry (e.g., 910*a*, 910*b*, 910*c* or 910*d*) different relative times of ingestion may be visually differentiated by color. In the scenario shown by manifest 900, each row of each intersecting entry may have a different colored background, with each different color indicating a different relative time of ingestion. For example, intersecting entry rows 915*a*-915*d* may have a specific background color corresponding to a "Morning", and intersecting entry rows 918*a*-918*d* may have a different background color corresponding to "Night." This visual differentiation may aid a user in easily determining the different relative times of ingestion.

Manifest 900 may indicate prescription 912*b* to be packaged into the every other individual receptacle of a bottom "Night" row 918*b*. Thus, prescription 912*b* may be mapped to be packaged for ingestion on every other night of the week. Manifest 900 may indicate prescription 912*d* to be packaged into only one individual receptacle in a "Morning" row 915*d* of the Week 1 container, to reflect the once a month dosing regime.

If, for example, prescription 912*b* and prescription 912*d* were not a part of the multi-dose medicament order represented by manifest 900, a different embodiment of a manifest (such as manifest 600 or manifest 100) may be used for the remaining combination of prescriptions (912*a*, 912*c*). By including the varying daily dosage of prescription 912*b* and 912*d* in the multi-dose medicament order, however, the entire combination of prescriptions (912*a*-912*d*) may be better served by the embodiment of manifest 900.

Of course, other embodiments of the manifest 900 are possible. For example, the manifest 900 may support any number of relative times of ingestion and/or any number of weeks. In some embodiments, containers 908*a*-908*d* may represent different relative times of ingestion instead of weeks, and rows (e.g., 915*a-c* and 918*a-c*) may represent different weeks instead of relative times of ingestion. Other embodiments or combinations of the manifest 900 are also possible.

Turning to FIG. 10, an embodiment of a manifest 1000 is illustrated. The multi-dose medicament order supported by manifest 1000 may include individual containers, each of which may contain more than one week's worth of medicaments. For example, individual container 1 (reference 1002) of manifest 1000 may contain medicaments for a Week 1 (1005) and a Week 2 (1008). Individual container 2 (reference 1010) may contain medicaments for a Week 3 (1012) and a Week 4 (1015). Each individual container may have a corresponding machine-readable container identifier, and each week included on each individual container may have a corresponding machine-readable week identifier. In one embodiment, an individual container may include a grid of individual receptacles, with one axis of the grid corresponding to a specific relative time of ingestion (e.g., "Morning," "Noon," "Night," "AM," "PM," etc.), the other axis of the grid corresponding to a specific day of a week (e.g., "Sunday," "Monday" etc.).

Generally, manifest 1000 may have characteristics similar to the other embodiments of the present disclosure (e.g., a prescription matrix and container matrix intersection, representations of individual medicaments of individual prescriptions, prescription attributes, total number of medicament units per individual receptacle, visual color differentiation, etc.). The manifest 1000 may support a fill pattern for dosing regimes that are constant for each day of a week, but that may vary from one week to another and/or vary from one relative time of ingestion to another. Furthermore, the manifest 1000 may represent multiple weeks in a single container. For example, as illustrated in manifest 1000, each individual receptacle mapped to be packaged with an assortment of medicaments to be ingested in the AM of Week 1 may include a total of seven units: one unit each of prescriptions 1018*a*, 1018*c*, 1018*d* and 1018*e*, and three units of prescriptions 1018*f*. Each individual receptacle mapped to be packaged with an assortment of medicaments to be ingested in the PM of Week 3 may include a total of eleven units: two units each of prescriptions 1018*a*, 1018*b* and 1018*d*, one unit of prescription 1018*e*, and four units of prescriptions 1018*f*. In this fashion, manifest 1000 may support a multi-dose medicament order having prescription(s) whose dosing regimes may remain constant for each day of a week, but may vary from one week to another or from one relative time of ingestion to another.

As in other embodiments, differences in dosing regimes may be differentiated, such as by color. For example, columns 1018*a*-1018*d* may have a background of one color to signify "AM," and columns 1020*a*-1020*d* may have a background of a different color to signify "PM." Also, other embodiments of the manifest 1000 may be possible. For example, any number of weeks may be represented on the manifest 1000. In some embodiments, weeks 1-4 may be included in a single card. In some embodiments, the manifest 1000 may support a 30 day supply of medicaments. Other embodiments or combination of embodiments of the manifest 1000 are also possible.

Several characteristics may be common to all embodiments of the present disclosure and may bear re-emphasizing. First, additional information may be included on embodiments of the manifest, including information such as store or pharmacy information, filling entity identification(s) and other information, prescribing entity information, dates of issue, ingestion dates or date ranges covered by the multi-dose medicament order and/or its associated containers, and the like. Secondly, any relative times of ingestion indicated on the manifest may be customizable. For example, a range of relative times of ingestion may not be limited to only the examples shown (i.e., "Morning(1)," "Morning(2)," "Evening," "AM," "PM," and "Night"). Relative times of ingestion may include actual clock times or other types of indications of relative times or time periods during a day.

Thirdly, some or all machine-readable identifiers on the manifest (e.g., order identifiers, container identifiers, prescription identifiers, assortment identifiers, etc.) may be co-derivable. For example, an order identifier may be derivable from a container identifier. A prescription identifier may be derivable from an assortment identifier. In some embodiments, derivability may be hierarchical, in some embodiments derivability may be mutual, and in some embodiments, a combination of hierarchical and mutual derivability of machine-readable identifiers may be possible.

Another characteristic common to the embodiments of the present disclosure may occur when the manifest contains an instance of an intersection of a prescription matrix and a container matrix that has too many columns or rows to fit on a single page or screen. In this situation, the instance of intersection may be split across multiple pages or screens, and may be identified accordingly.

Additionally, visual differentiation between different dosing regimes may be possible for any embodiment of the disclosure, irrespective of whether individual containers of the multi-dose medicament order correspond to weeks, to relative times of ingestions, or to some other categorization. Take the example of a desired differentiation by color of relative times of ingestion. In the embodiment of manifest 100 of FIG. 1, each individual container may be color-coded corresponding to different relative times of ingestion. In the embodiment of manifest 900 of FIG. 9, each row within each weekly container may be color-coded corresponding to different relative times of ingestion. Of course, for any embodiment of the disclosure, differentiation may not be limited to only differentiation between relative times of ingestion or dosing regime characteristics, but may differentiate between other characteristics or combinations of characteristics, such as patient preference, instructions for ingestion (e.g., take with food/water/on empty stomach), a week number or other calendar-type designation, and the like. Also, visual differentiation may not be limited to color-coding, but may use other types of differentiation such as font sizes or colors, dynamic representations on a screen or user display (such as blinking, flashing, graying-out and the like) or other types of differentiation.

A pictorial representation of an individual medicament may also be common to embodiments of the present disclosure. A pictorial representation may be a photographic, iconic or drawing representation. A pictorial representation may include a view of the front of the medicament and a view of the back of a medicament. Alternatively or additionally, a representation of the individual medicament may be alphanumeric, or may be both alphanumeric and pictorial.

Further, although the examples of the present disclosure illustrate embodiments of manifests and matrices in a given orientation, these illustrated orientations are not meant to be limiting. Any orientations of manifests and/or matrices may be possible. For example, in manifest 100 of FIG. 1, the prescription matrix 102 may be illustrated as having a generally horizontal orientation, and the container matrix 105 may be illustrated as having a generally vertical orientation. In a different embodiment of manifest 100, the prescription matrix 102 may have a generally vertical orientation and container matrix 105 may have a generally horizontal orientation. In another example, in manifest 900 of FIG. 9, an intersecting entry of the prescription matrix 902 and the container matrix 905 may be depicted as having rows corresponding to a relative time of ingestion, and columns corresponding to a day of the week. In a different embodiment of manifest 900, the rows of an intersecting entry may correspond to a day of the week, and the columns may correspond to a relative time of ingestion. Other orientation variations for the disclosed embodiments may be possible.

Indeed, in some embodiments, a manifest and/or matrix therein may not even have an "orientation." For instance, in a high-speed automated filling machine, the manifest may be embodied entirely on a computing entity in software, and may not be displayed to a user at all.

The aforementioned scenarios are exemplary and not intended to cover the complete set of systems that may use a manifest for filling a multi-dose medicament order. One of ordinary skill in the art may easily apply the aforementioned system 400 and methods to multiple varieties of scenarios of filling a multi-dose medicament order, whether manual, semi-automatic or automatic, local or remote.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed:

1. A computing device for a multi-dose medicament container fill, comprising:
   a processor;
   a memory; and
   computer-executable instructions stored on the memory and executable by the processor to:
      generate a manifest, the manifest comprising a representation of at least two matrices that intersect, the representation corresponding to a multi-dose medicament order to be filled, the at least two matrices including:
         a prescription matrix corresponding to a set of prescriptions of the multi-dose medicament order; and
         a container matrix corresponding to a set of containers of the multi-dose medicament order, wherein each container of the set of containers is divided into individual receptacles,
      wherein each intersecting entry of the at least two matrices has an indication of a number of medicaments of an individual prescription from the set of prescriptions to be packaged into a receptacle from the set of containers, and at least one receptacle is to be packaged with medicaments of at least two individual prescriptions; and
   store the manifest in a data storage entity: and
   fill the multi-dose medicament order, including at least one of:
      initiate printing corresponding to the multi-dose medicament order, including electronically sending, by the computing device to a printing entity, at least a first portion of information of the manifest;

initiate selecting at least one medicament inventory holder containing a portion of an inventory of a medicament corresponding to one of the set of prescriptions of the multi-dose medicament order, including electronically sending, by the computing device to a picking entity, at least a second portion of the information of the manifest; or initiate verifying the multi-dose medicament order, including electronically sending, by the computing device to a verification entity, at least a third portion of the information of the manifest.

2. The computing device of claim 1, wherein the indication of the number of medicaments included in the representation is pictorial.

3. The computing device of claim 1,
wherein the prescription matrix included in the representation includes: a first prescription axis having a row corresponding to each individual prescription from the set of prescriptions, a row dimension of the prescription matrix equal to a total number of individual prescriptions in the set of prescriptions, and a second prescription axis having a column corresponding to each of a set of prescription attributes; and wherein the container matrix included in the representation includes:
a first container axis having a row corresponding to each individual prescription from the set of prescriptions, and
a second container axis having a column corresponding to each individual container, a column dimension of the container matrix equal to a total number of individual containers in the set of containers.

4. The computing device of claim 3, wherein the representation includes a transposition of the first prescription axis and the second prescription axis and the representation further includes a transposition of the first container axis and the second container axis.

5. The computing device of claim 3, wherein the set of prescription attributes included in the representation includes at least one of:
an Rx number,
at least one of: a medication name in textual form or an NDC number,
an image;
a description;
dosing instructions,
a total number of units,
at least one legally required fill attribute,
a lot number,
an expiration date,
a machine-readable individual prescription identifier, or
an indication of each individual container of the set of containers.

6. The computing device of claim 5, wherein the set of prescription attributes included in the representation further includes an individual prescription approval.

7. The computing device of claim 3, wherein each column of the second container axis included in the representation includes an individual container approval field.

8. The computing device of claim 1, wherein the representation further comprises at least one of:
a machine-readable order identifier for the multi-dose medicament order, a machine-readable prescription identifier for each individual prescription from the set of prescriptions, the machine-readable prescription identifier included in the prescription matrix, and a machine-readable container identifier for each individual container from the set of containers, the machine-readable container identifier included in the container matrix.

9. The computing device of claim 8, wherein the machine-readable order identifier, the machine-readable prescription identifier and the machine-readable container identifier included in the representation each has an accuracy check attribute.

10. The computing device of claim 8, wherein the machine-readable container identifier is derivable from the machine-readable order identifier, and the machine-readable prescription identifier is derivable from the machine-readable order identifier.

11. The computing device of claim 8, wherein if each intersecting entry of the at least two matrices included in the representation has an indication of one or more medicaments, a machine-readable prescription identifier for a specific prescription corresponding to each intersecting entry and a machine-readable container identifier for a specific container corresponding to each intersecting entry are associated.

12. The computing device of claim 1, wherein each container of the set of containers included in the representation corresponds to at least one dosing regime attribute, the at least one dosing regime attribute selected from a group of dosing regime attributes including: a time period of day, a time of day, a week, a month, a date, a characteristic of a medicament, and a user selection.

13. The computing device of claim 12, further comprising a user interface, and wherein at least one of the at least one dosing regime attribute is visually differentiated on a presentation of the manifest on the user interface.

14. The computing device of claim 13, wherein the at least one of the at least one dosing regime attribute is represented by a unique color on the presentation of the manifest.

15. The computing device of claim 1, wherein at least one of:
the manifest includes a set of instances of the representation of the at least two matrices that intersect, with each instance of the set of instances including the prescription matrix and an individual container matrix corresponding to a specific individual container from the set of containers, or the each intersecting entry of the at least two matrices has an indication of a number of medicaments of the individual prescription from the set of prescriptions to be packaged into an individual receptacle of the individual container from the set of containers.

16. A method for creating a manifest for a multi-dose medicament container fill, comprising:
obtaining, at a computer, prescription information for each individual prescription from a set of prescriptions for a multi-dose medicament order to be filled;
obtaining, at the computer, container information for each individual container of a set of containers for the multi-dose medicament order;
generating, by the computer, the manifest for the multi-dose medicament order, the manifest comprising a representation of at least two matrices that intersect, the at least two matrices including:
a prescription matrix corresponding to the set of prescriptions, and a container matrix corresponding to the set of containers, wherein each container of the set of containers is divided into individual receptacles, wherein each intersecting entry of the at least two matrices has an indication of a number of medicaments of an individual prescription to be packaged into an individual container, and at least one receptacle is to be packaged with medicaments of at least two individual prescriptions; and wherein at least one dimension of the prescription matrix is unequal to a corresponding dimension of the container matrix;

displaying the manifest on a user interface; and filling the multi-dose medicament order, including at least one of:

initiating printing corresponding to the multi-dose medicament order, including electronically sending, by the computer to a printing entity, at least a first portion of the information of the manifest;

initiating selecting at least one medicament inventory holder containing a portion of an inventory of a medicament corresponding to one of the set of prescriptions of the multi-dose medicament order, including electronically sending, by the computer to a picking entity, at least a second portion of the information of the manifest; or initiating verifying the multi-dose medicament order, including electronically sending, by the computer to a verification entity, at least a third portion of the information of the manifest.

17. The method of claim 16, wherein displaying the manifest on the user interface comprises at least one of: displaying the manifest on a user interface of the computer, sending the manifest to a different computing device for display on a user interface of the different computing device, or sending the manifest to a printing device.

18. The method of claim 16, wherein generating the manifest comprises generating the manifest with a pictorial representation of the indication of the number of medicaments.

19. The method of claim 16, wherein generating the manifest comprises:

generating a first prescription axis of the prescription matrix having a row corresponding to each individual prescription, a row dimension of the prescription matrix equal to a total number of individual prescriptions in the set of prescriptions;

generating a second prescription axis of the prescription matrix having a column corresponding to each of a set of prescription attributes;

generating a first container axis of the container matrix having a row corresponding to each individual prescription; and generating a second container axis of the container matrix having a column corresponding to each individual container, a column dimension of the container matrix equal to a total number of individual containers in the set of containers.

20. The method of claim 19, wherein the first prescription axis and the second prescription axis are transposed and wherein the first container axis and the second container axis are transposed.

21. The method of claim 19, wherein generating the manifest comprises generating the manifest with the prescription matrix including the column corresponding to each of the set of prescription attributes and the set of prescription attributes includes at least one of:

an Rx number, at least one of: a medication name in textual form or an NDC number, dosing instructions, an image;

a description;

a total number of units, at least one legally required fill attribute, a lot number, an expiration date, a machine-readable individual prescription identifier, or an indication of each individual container of the set of containers.

22. The method of claim 19, wherein generating the manifest comprises at least one of:

generating the column corresponding to each of the set of prescription attributes, wherein the set of prescription attributes includes an individual prescription approval;

generating the column corresponding to each individual container, wherein the column corresponding to each individual container includes an individual container approval field; or generating an order approval field.

23. The method of claim 16, wherein generating the manifest further comprises at least one of:

generating, by the computer, a machine-readable order identifier for the multi-dose medicament order, generating, by the computer, a machine-readable prescription identifier for each individual prescription, the machine-readable prescription identifier included in the prescription matrix, or generating, by the computer, a machine-readable container identifier for each individual container, the machine-readable container identifier included in the container matrix; and wherein displaying the manifest further comprises displaying at least one of the machine-readable order identifier, the machine-readable prescription identifier, or the machine-readable container identifier.

24. The method of claim 23, wherein generating the machine-readable order identifier, the machine-readable prescription identifier and the machine-readable container identifier comprises generating the machine-readable order identifier, the machine-readable prescription identifier and the machine-readable container identifier each with an accuracy check attribute.

25. The method of claim 23, wherein generating the machine-readable container identifier comprises generating a machine-readable container identifier that is derivable from the machine-readable order identifier, wherein generating the machine-readable prescription identifier comprises generating a machine-readable identifier that is derivable from the machine-readable order identifier, and wherein if each intersecting entry of the at least two matrices has an indication of one or more medicaments, generating a machine-readable prescription identifier for a specific prescription corresponding to each intersecting entry comprises generating a machine-readable prescription identifier associated with a machine-readable container identifier for a specific container corresponding to each intersecting entry.

26. The method of claim 16, wherein generating the manifest comprises generating the container matrix corresponding to the set of containers wherein:

each individual container of the set of containers corresponds to at least one dosing regime attribute, the at least one dosing regime attribute selected from a group of dosing regime attributes including: a time period of day, a time of day, a week, a month, a date, a characteristic of a medicament, and a user selection.

27. The method of claim 26, wherein displaying the manifest on the user interface comprises representing the at least one of the at least one dosing regime attribute on the manifest by a unique visual differentiation.

28. A method of filling, based on a single manifest, a multi-dose medicament order in a system, comprising:
electronically obtaining, at a computing device of the system, the single manifest, the single manifest being a representation of at least two matrices that intersect and corresponding to the multi-dose medicament order, and the at least two matrices including:
a prescription matrix corresponding to a set of prescriptions of the multi-dose medicament order including:
a first prescription axis having a row corresponding to each individual prescription from the set of prescriptions, a row dimension of the prescription matrix equal to a total number of individual prescriptions in the set of prescriptions, and
a second prescription axis having a column corresponding to each of a set of prescription attributes; and
a container matrix corresponding to a set of containers of the multi-dose medicament order, wherein each container of the set of containers is divided into individual receptacles, the container matrix including:
a first container axis having a row corresponding to each individual prescription from the set of prescriptions, and
a second container axis having a column corresponding to each individual container, a column dimension of the container matrix equal to a total number of individual containers in the set of containers;
wherein:
each intersecting entry of the at least two matrices has an indication of a number of medicaments of an individual prescription from the set of prescriptions mapped to be packaged into a receptacle from the set of containers, and
at least one receptacle is to be packaged with medicaments of at least two individual prescriptions; and
filling the multi-dose medicament order, including at least one of:
initiating printing corresponding to the multi-dose medicament order, including electronically sending, by the computing device to a printing entity of the system, at least a first portion of the information of the manifest;
initiating selecting at least one medicament inventory holder containing a portion of an inventory of a medicament corresponding to one of the set of prescriptions of the multi-dose medicament order, including electronically sending, by the computing device to a picking entity of the system, at least a second portion of the information of the manifest; or
initiating verifying the multi-dose medicament order, including electronically sending, by the computing device to a verification entity of the system, at least a third portion of the information of the manifest.

29. The method of claim 28, wherein the first prescription axis and the second prescription axis are transposed, and wherein the first container axis and the second container axis are transposed.

30. The method of claim 28, wherein electronically obtaining the single manifest further comprises electronically obtaining:
a machine-readable prescription identifier for each individual prescription included in the set of prescription attributes,
a machine-readable container identifier for each individual container included in the container matrix, and
a machine-readable order identifier corresponding to the single manifest.

31. The method of claim 30, wherein at least one of:
each machine-readable prescription identifier is derivable from the machine-readable order identifier,
each machine-readable container identifier is derivable from the machine-readable order identifier,
each machine-readable container identifier is associated with each machine-readable prescription identifier of the single manifest, or
each machine-readable prescription identifier, each machine-readable container identifier, and the machine-readable order identifier each has an accuracy check attribute.

32. The method of claim 28, wherein initiating the printing corresponding to the multi-dose medicament order further includes determining the at least the first portion of the information of the manifest from at least one entry of one of the at least two matrices of the single manifest.

33. The method of claim 32, further comprising printing, by the printing entity and based on the at least the first portion of the information of the manifest, at least one of: a dosing regime, dosing instructions, evidence of registered pharmacist approval, warnings, precautions, prescription labels, or labels including legally required content.

34. The method of claim 28, wherein initiating the selecting of the at least one medicament inventory holder further includes determining the at least the second portion of the information of the manifest, including for a specific receptacle of the multi-dose medicament order:
determining a number of medicament units of a specific prescription to be packaged into the specific receptacle based on a number of medicaments of the specific prescription indicated in an intersecting entry of a specific row of the prescription matrix corresponding to the specific prescription and a specific column of the container matrix corresponding to the specific receptacle.

35. The method of claim 34, further comprising selecting, by the picking entity and based on the determined number of medicament units, at least one medicament inventory holder corresponding to the specific prescription from a group of medicament inventory holders including: an intermediate inventory container, a pre-filled inventory container, or a medicament inventory container.

36. The method of claim 28, wherein the verifying of the multi-dose medicament order comprises:
verifying, by the verification entity, a filled container of a filled, multi-dose medicament order, wherein the filled container is verified as being correct if a number of medicaments of each individual prescription packaged into the filled container matches a number of medicaments of each individual prescription indicated in a column of the container matrix of the single manifest corresponding to the filled container;

verifying, by the verification entity, a specific prescription of the filled, multi-dose medicament order, wherein the specific prescription is verified as being correct:
    if a number of medicaments of the specific prescription packaged into each filled container of the filled, multi-dose medicament order matches a number of medicaments of the specific prescription mapped to each filled container as indicated in a row of the prescription matrix of the single manifest corresponding to the specific prescription, and
    if a set of prescription attributes of the packaged number of medicaments matches a set of prescription attributes indicated in the row of the prescription matrix corresponding to the specific prescription; or
verifying, by the verification entity, the filled, multi-dose medicament order, wherein the filled, multi-dose medicament order is verified as being correct if each filled container or each specific prescription of the multi-dose medicament order is verified as being correct.

37. The method of claim 36, further comprising at least one of:
    electronically obtaining electronically an indication of container approval in a container approval field of the column corresponding to the filled container if the filled container is verified as being correct;
    electronically obtaining an indication of prescription approval in a prescription approval field of the row corresponding to the specific prescription if the specific prescription is verified as being correct, or
    electronically obtaining an indication of order approval in an order approval field of the single manifest if the filled, multi-dose medicament order is verified as being correct.

38. A system for filling a multi-dose medicament order using a manifest, the system comprising:
    a single manifest corresponding to a multi-dose medicament order to be filled, the multi-dose medicament order including an indication of a set of prescriptions to be packaged together; and
    a computer operable to:
        receive the single manifest;
        exhibit the single manifest on a display; and
        initiate filling of the multi-dose medicament order, including at least one of:
            initiate printing corresponding to the multi-dose medicament order, including electronically sending, by the computer to a printing entity of the system, at least a first portion of the information of the manifest,
            initiate selecting at least one medicament inventory holder containing a portion of an inventory of a medicament corresponding to one of the set of prescriptions of the multi-dose medicament order, including electronically sending, by the computer to a picking entity of the system, at least a second portion of the information of the manifest, or
            initiating verifying the multi-dose medicament order, including electronically sending, by the computer to a verification entity of the system, at least a third portion of the information of the manifest,
    wherein the single manifest comprises a representation of at least two matrices that intersect, the representation corresponding to the multi-dose medicament order to be filled, and the at least two matrices including:
        a prescription matrix corresponding to the set of prescriptions of the multi-dose medicament order, including:
            a first prescription axis having a row corresponding to each individual prescription from the set of prescriptions, a row dimension of the prescription matrix equal to a total number of individual prescriptions in the set of prescriptions, and
            a second prescription axis having a column corresponding to each of a set of prescription attributes; and
        a container matrix corresponding to a set of containers of the multi-dose medicament order, wherein each container of the set of containers is divided into individual receptacles, the container matrix including:
            a first container axis having a row corresponding to each individual prescription from the set of prescriptions, and
            a second container axis having a column corresponding to each individual container, a column dimension of the container matrix equal to a total number of individual containers in the set of containers;
    wherein:
        each intersecting entry of the at least two matrices has an indication of a number of medicaments of an individual prescription from the set of prescriptions to be packaged into a receptacle from the set of containers,
        at least one receptacle is to be packaged with medicaments of at least two individual prescriptions, and
        the single manifest includes a machine-readable identifier.

39. The system of claim 38, wherein the machine-readable identifier includes at a least one of: a machine-readable prescription identifier corresponding to each individual prescription, a machine-readable container identifier corresponding to each individual container, or a machine-readable order identifier.

40. The system of claim 38, wherein the computer is further operable to generate the single manifest.

41. The system of claim 38, wherein the computer is at least one of: a storage entity, the picking entity, a filling entity, and the verification entity.

42. The system of claim 38, wherein the single manifest further comprises at least one of: a prescription approval field in the prescription matrix for each individual prescription, a container approval field in the container matrix for each individual container, or an order approval field.

43. The system of claim 38, wherein the single manifest includes a set of instances of the representation of the at least two matrices that intersect, with each instance of the set of instances including the prescription matrix and an individual container matrix corresponding to a specific receptacle from the set of containers.

44. The system of claim 38, wherein the first prescription axis and the second prescription axis are transposed and wherein the first container axis and the second container axis are transposed.

* * * * *